(12) United States Patent
    Severino

(10) Patent No.: US 10,105,074 B2
(45) Date of Patent: *Oct. 23, 2018

(54) SYSTEM AND METHOD FOR VISUALIZING ELECTROPHYSIOLOGY DATA

(71) Applicant: Biosense Webster (Israel) Ltd., Yokneam (IL)

(72) Inventor: Thomas Michael Severino, Baltimore, MD (US)

(73) Assignee: Biosense Webster (Israel) Ltd., Yokneam (IL)

(*) Notice: Subject to any disclaimer, the term of this patent is extended or adjusted under 35 U.S.C. 154(b) by 0 days.

This patent is subject to a terminal disclaimer.

(21) Appl. No.: 15/499,854

(22) Filed: Apr. 27, 2017

(65) Prior Publication Data

US 2017/0231517 A1 Aug. 17, 2017

Related U.S. Application Data

(63) Continuation of application No. 14/587,964, filed on Dec. 31, 2014, now Pat. No. 9,662,033.

(51) Int. Cl.
*A61B 5/044* (2006.01)
*A61B 5/04* (2006.01)
(Continued)

(52) U.S. Cl.
CPC .......... *A61B 5/044* (2013.01); *A61B 5/04012* (2013.01); *A61B 5/0422* (2013.01); *A61B 5/0432* (2013.01); *A61B 5/7246* (2013.01)

(58) Field of Classification Search
None
See application file for complete search history.

(56) References Cited

U.S. PATENT DOCUMENTS 5,391,199 A    2/1995   Ben-Haim
5,443,489 A    8/1995   Ben-Haim
                (Continued)

FOREIGN PATENT DOCUMENTS

CA        2018215 A1   4/1995
WO     WO 95/10225    4/1995

OTHER PUBLICATIONS

Extended European Search Report for EP15202606.8, dated Sep. 26, 2016, 10 pages.

*Primary Examiner* — Erica Lee
(74) *Attorney, Agent, or Firm* — Lewis Roca Rothgerber Christie LLP

(57) ABSTRACT

A method and system for visualization of electrophysiology information sensed by electrodes on a catheter, includes recording times of electrode signal acquisition, designating a reference electrode signal acquisition, assigning a relative time to each recorded time of electrode signal acquisition relative to the reference electrode signal acquisition, identifying the electrodes with signal acquisition, correlating assigned relative times to identified electrodes to generate a sequence of electrode signal acquisitions, and generating a visual representation of the sequence of electrode signal acquisitions generating a visual representation with a graphical image of the electrodes, wherein individual electrodes are visually marked to represent the sequence of electrode signal acquisitions.

18 Claims, 31 Drawing Sheets

(9 of 31 Drawing Sheet(s) Filed in Color)

(51) Int. Cl.
    *A61B 5/00*     (2006.01)
    *A61B 5/0432*   (2006.01)
    *A61B 5/042*    (2006.01)

(56) References Cited

U.S. PATENT DOCUMENTS

| | | |
|---|---|---|
| 5,558,091 A | 9/1996 | Acker et al. |
| 5,944,022 A | 8/1999 | Nardella et al. |
| 5,983,126 A | 11/1999 | Wittkampf |
| 6,157,855 A | 12/2000 | Sjoholm |
| 6,172,499 B1 | 1/2001 | Ashe |
| 6,177,792 B1 | 1/2001 | Govari et al. |
| 6,226,542 B1 | 5/2001 | Reisfeld |
| 6,301,496 B1 | 10/2001 | Reisfeld |
| 6,456,864 B1 | 9/2002 | Swanson et al. |
| 6,690,963 B2 | 2/2004 | Ben-Haim et al. |
| 6,788,967 B2 | 9/2004 | Ben-Haim et al. |
| 6,814,733 B2 | 11/2004 | Schwartz et al. |
| 6,892,091 B1 | 5/2005 | Ben-Haim et al. |
| 6,997,924 B2 | 2/2006 | Schwartz et al. |
| 7,156,816 B2 | 1/2007 | Schwartz et al. |
| 7,536,218 B2 | 5/2009 | Govari et al. |
| 8,478,383 B2 | 7/2013 | Bar-Tal et al. |
| 8,577,450 B1 | 11/2013 | Chmiel et al. |
| 2002/0055674 A1 | 5/2002 | Ben-Haim et al. |
| 2004/0220635 A1 | 11/2004 | Burnes |
| 2013/0218223 A1 | 8/2013 | Ghosh et al. |
| 2015/0073246 A1* | 3/2015 | Chmiel .............. A61B 18/1492 600/374 |
| 2015/0119738 A1 | 4/2015 | Deno |

* cited by examiner

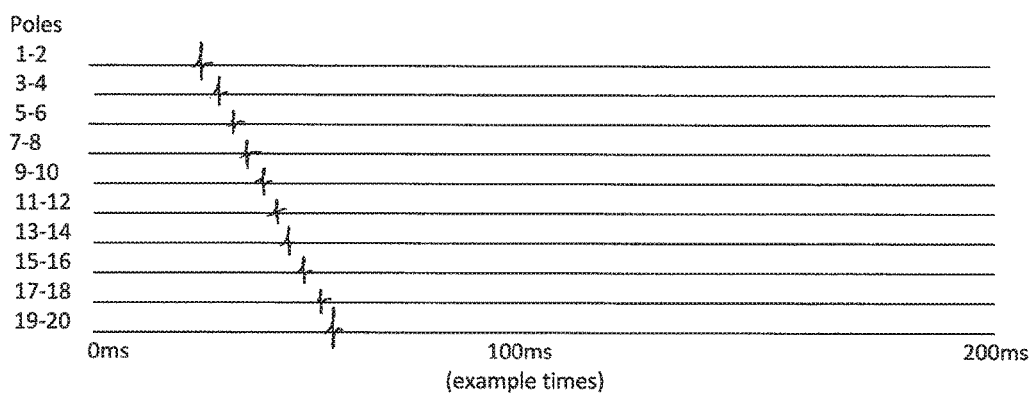
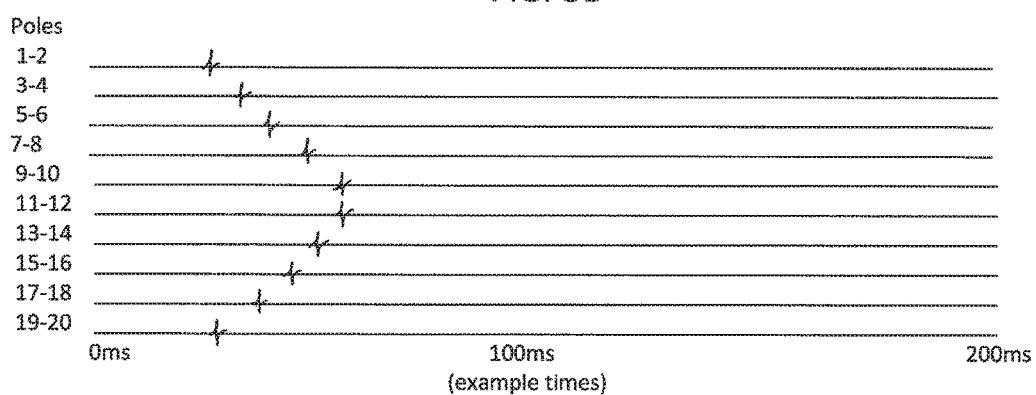

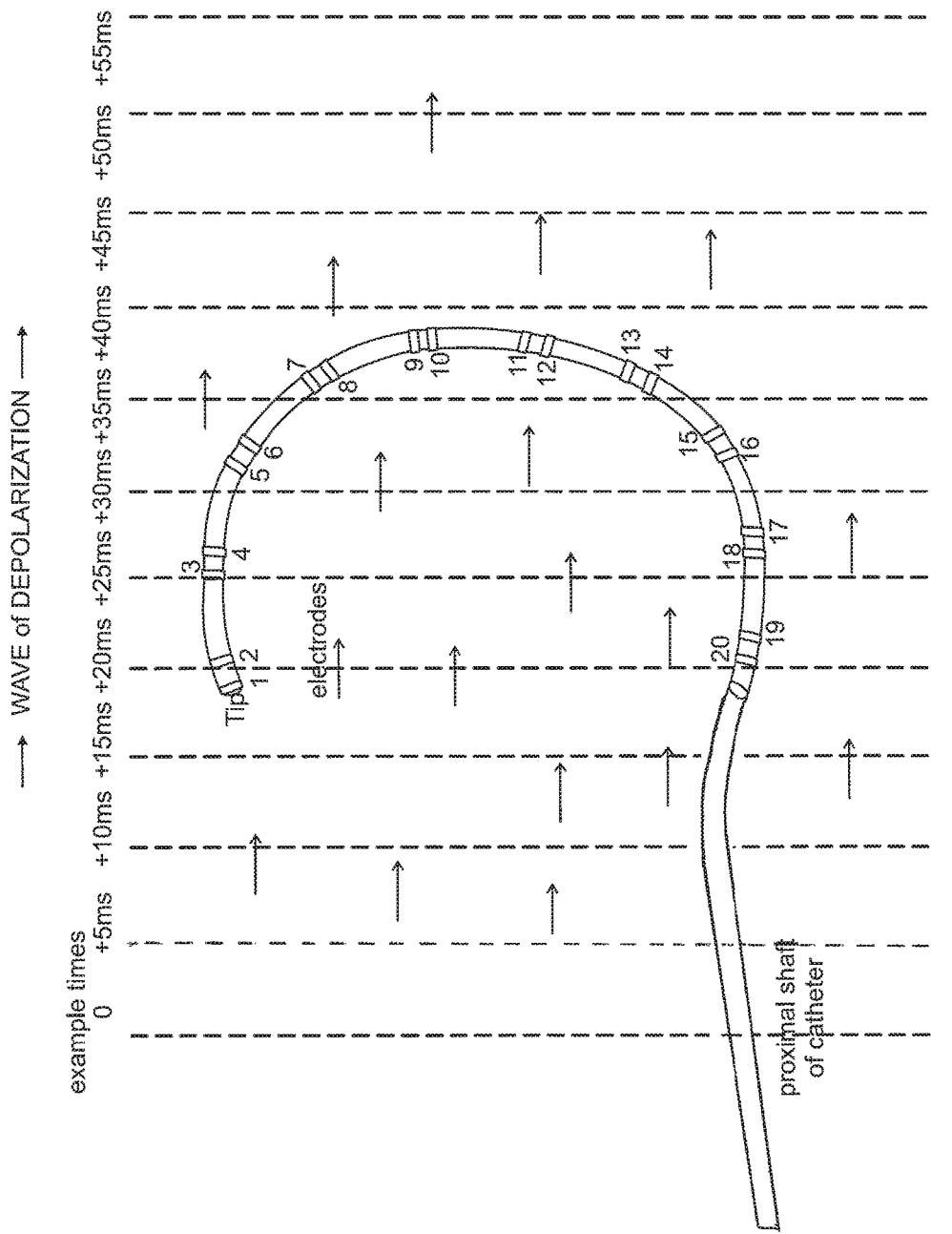

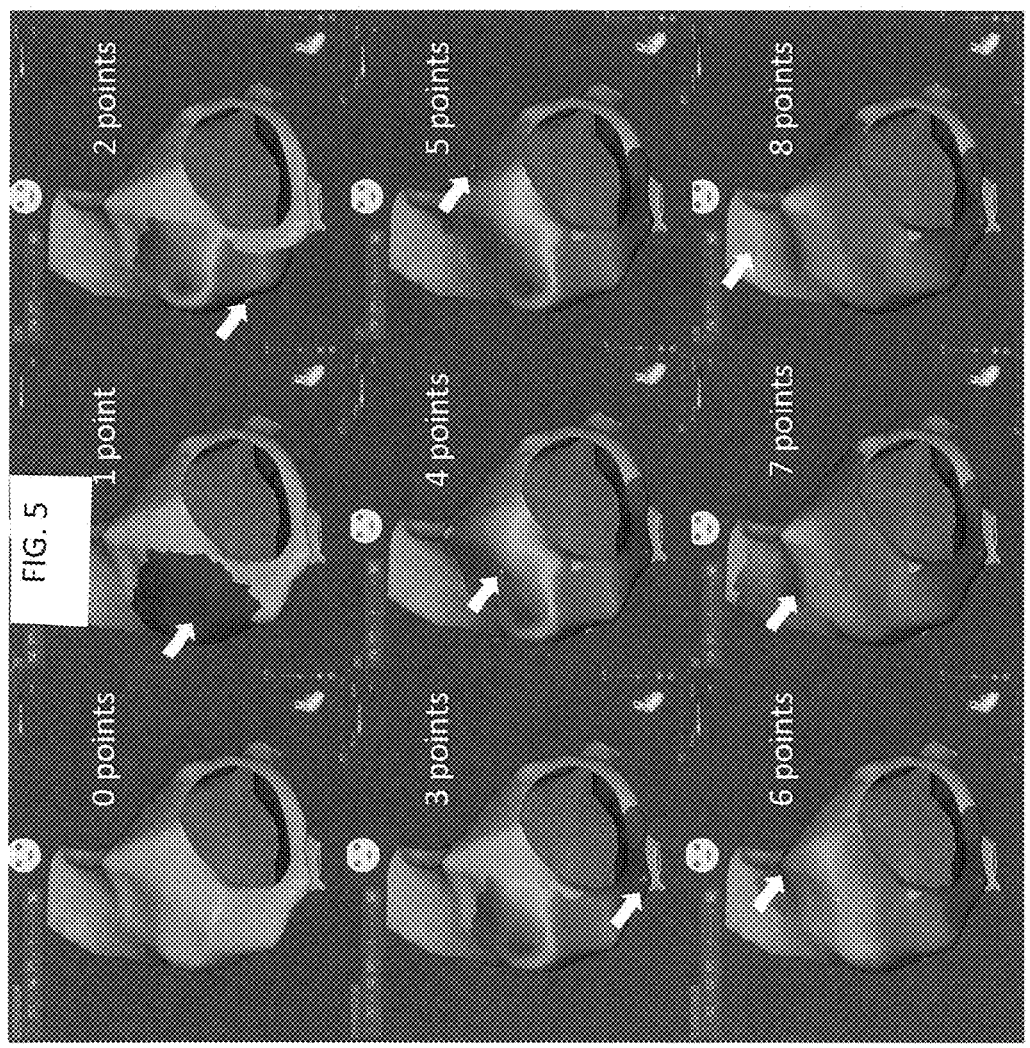

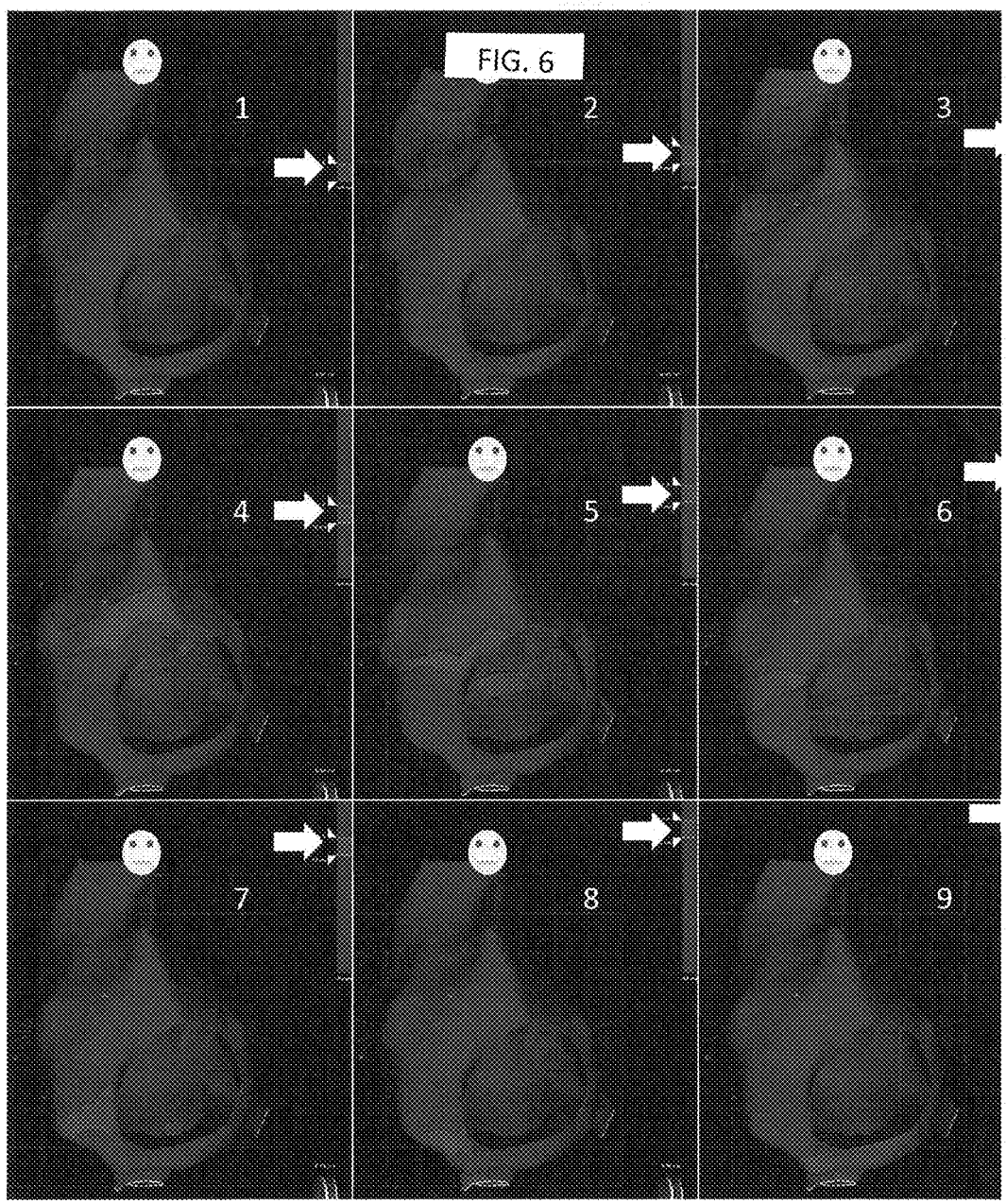

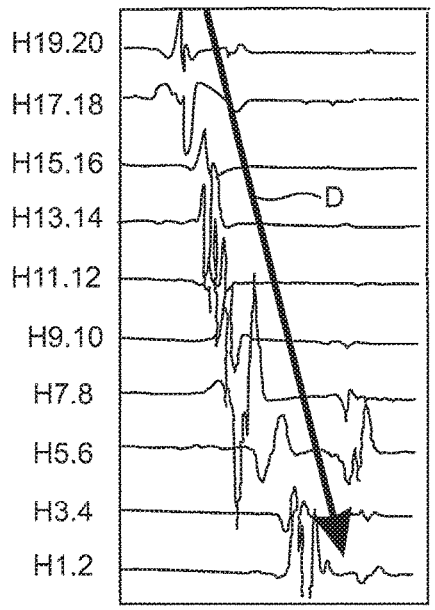 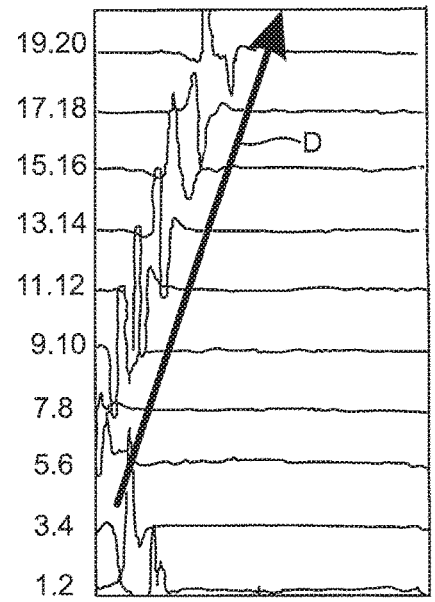
FIG. 9A  FIG. 9B
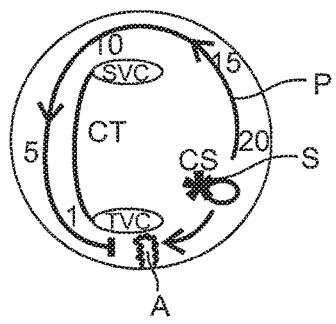 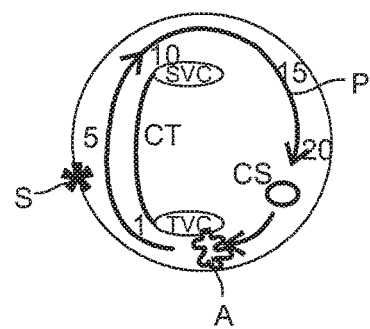
FIG. 10A  FIG. 10B

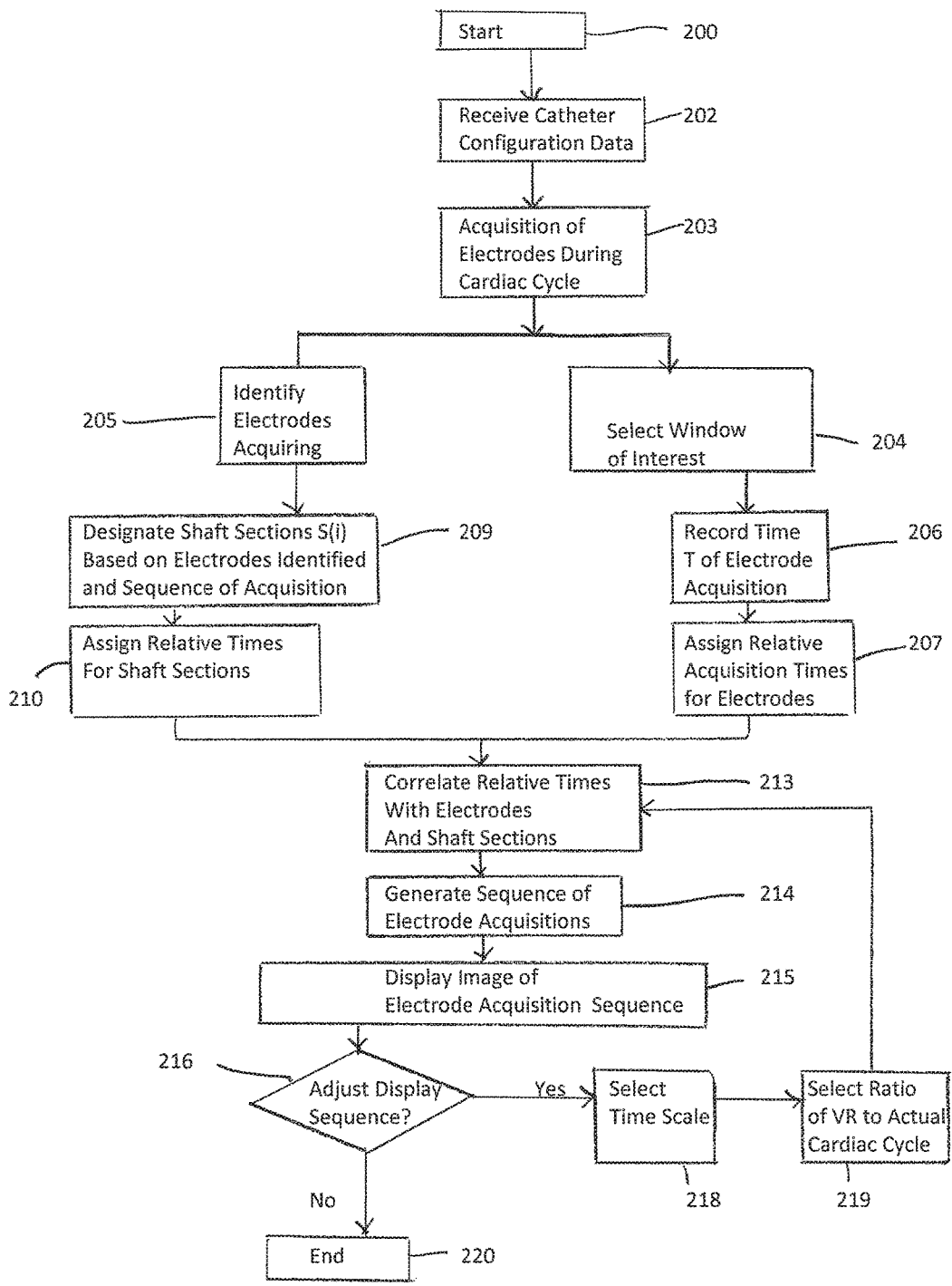

FIG. 18A

| Record Time t(i) (Block 206) | Assign Relative Time T(i) (Block 207) | Identify Pole(s) P(i) (Block 205) | Correlate Pole with Relative Time (Block 214) | Display Sequence (Block 215) |
|---|---|---|---|---|
| t(a) = 1.015s | T(a) | 1 | Pole 1 = 0ms | a |
| t(b) = 1.016s | T(b) | 2 | Pole 2 = +1ms | b |
| t(c) = 1.018s | T(c) | 3 | Pole 3 = +3ms | c |
| t(d) = 1.019s | T(d) | 4 | Pole 4 = +4ms | d |
| t(e) = 1.021s | T(e) | 5 | Pole 5 = +6ms | e |

FIG. 18B

| Record Time t(i) (Block 206) | Assign Relative Time T(i) (Block 207) | Identify Pole(s) P(i) (Block 205) | Correlate Pole with Relative Time (Block 214) | Display Sequence (Block 215) |
|---|---|---|---|---|
| t(a) = 1.015s | T(a) | 3 | Pole 3 = 0ms | a |
| t(b) = 1.016s | T(b) | 4 and 2 | Pole 2 = Pole 4 = +1ms | b |
| t(c) = 1.018s | T(c) | 5 and 1 | Pole 1 = Pole 5 = +3ms | c |

FIG. 18C

| Correlate Pole P(i) and Relative Time T(i) (Block 214) | Adjustment scale factor N (Block 218) | Re-Correlate (Block 214) |
|---|---|---|
| Pole 1 = 0ms | N=10 | Pole 1 = 0ms |
| Pole 2 = +1ms | N=10 | Pole 2 = +10ms |
| Pole 3 = +3ms | N=10 | Pole 3 = +30ms |
| Pole 4 = +4ms | N=10 | Pole 4 = +40ms |
| Pole 5 = +6ms | N=10 | Pole 5 = +60ms |

FIG. 18D

| Record time t(i) (Block 206) | Assign relative time T(i) for Pole(s) (Block 207) | Identify Pole(s) P(i) (Block 205) | Designate Shaft Section(s) S(i) (Block 209) | Assign relative time T(i) for Shaft Section(s) (Block 210) | Correlate Pole/Shaft with Relative Time T(i) (Block 214) | Display Sequence (Block 215) |
|---|---|---|---|---|---|---|
| t(a) = 1.015 s | T(a) = 0ms | 3 | | | P3 = 0ms | a |
| t(b) = 1.016 s | T(b) =+1ms | 4 and 2 | | | P4 = P2 = +1ms | c |
| | | | S3 and S2 | T = +0.5ms | S3 = S2 =0.5ms | b |
| t(c) = 1.17s | T(c) =+2ms | 5 | | | P5= +2ms | e |
| | | | S4 | T = +1.5ms | S4= +1.5ms | d |
| t(d) = 1.18s | T(d) =+3ms | 1 | | | P1 = +3ms | g |
| | | | S3 | T = +3.5ms | S1 = +2.5ms | f |

FIG. 18E

| Record Acquisition time $t_i$ | Assign relative time $T_i$ for Pole | Identify Pole(s) Pi | Designate Shaft Section(s) S(i) | Assign relative time T for Shaft Section(s) | Correlate Pole/Shaft with Relative Time T(i) (Block 214) | Display Sequence (Block 215) |
|---|---|---|---|---|---|---|
| t(a) = 1.015 s | T(a) = 0ms | 3 | | | P3 = 0ms | a |
| t(b) = 1.016 s | T(b) =+1ms | 4 and 2 | | | P2 = P4 = +1ms | e |
| | | | S3a and S2c | T= +0.25s | S3a = S2c=+0.25s | b |
| | | | S3b and S2b | T= +0.50 s | S3b=S2b = +0.50s | c |
| | | | S3c and S2a | T= +0.75s | S3c=S2a=+0.75s | d |
| t(c) = 1.17 s | T(c) =+2ms | 5 and 1 | | | P5=P1=+2ms | i |
| | | | S4a and S1c | T = +1.25s | S4a=S1c=+1.25s | f |
| | | | S4b and S2b | T= +1.50s | S4b=S2b=+1.50s | g |
| | | | S4c and S2a | T = +1.75s | S4c=S2a=+1.75s | h |

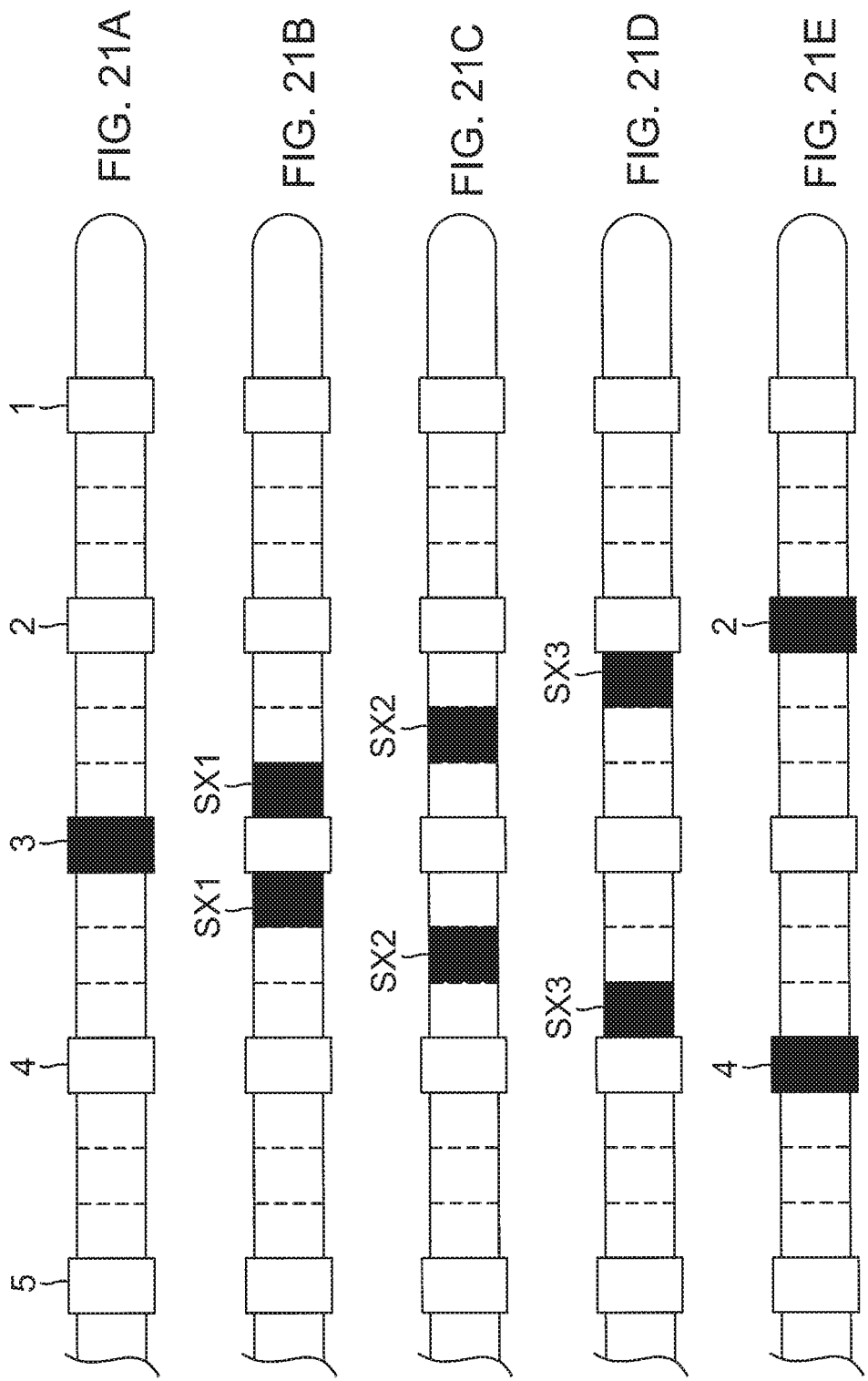

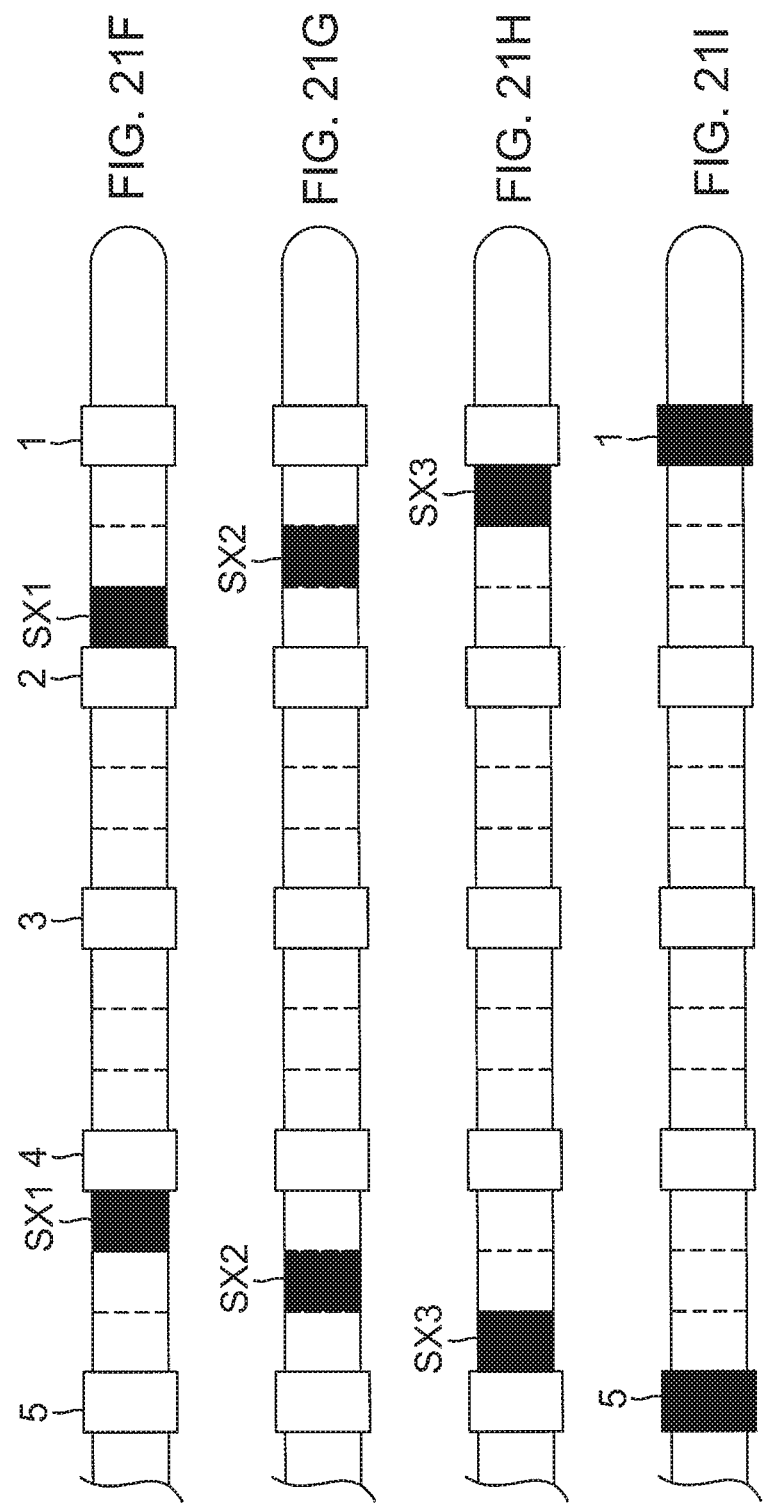

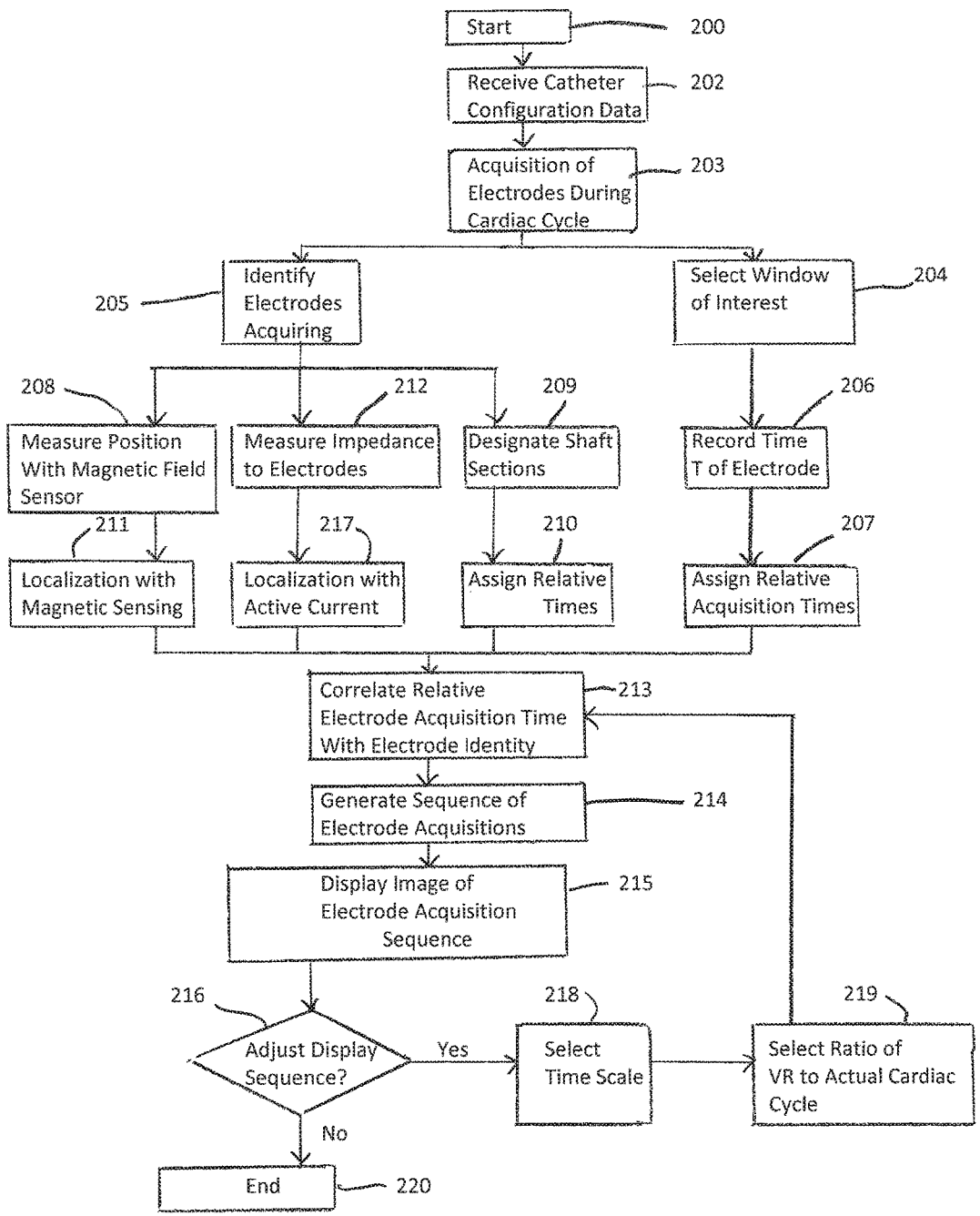

SYSTEM AND METHOD FOR VISUALIZING ELECTROPHYSIOLOGY DATA

CROSS REFERENCE TO RELATED APPLICATION(S)

This application is a continuation of U.S. patent application Ser. No. 14/587,964, filed Dec. 31, 2014, the entire content of which is incorporated herein by reference.

FIELD OF THE INVENTION

This invention relates generally to visualization of electrical activity of a patient, and more particularly to spatial visualization of electrophysiology data for a patient as detected by a catheter.

BACKGROUND

Cardiac arrhythmias are the leading cause of death in the United States. Normally, electrical acquisition signals are conducted in an orderly way through the atrium and into the ventricle, passing each point in the heart only once in each heart cycle. Electrical acquisition signals at different locations in the heart are well correlated, taking into account normal propagation delays from one region of the heart to another. In response to local activation signals, the atrial muscle fibers contract in proper synchrony to pump blood through the atrium.

The electrical conduction system of the heart provides the rhythm, or sequence of contraction of the heart muscle, so it may most efficiently pump blood to the rest of the body. Electrophysiologists study the conduction system to diagnose and treat abnormal heart rhythms, known as arrhythmias. It is desirable to provide methods and equipment that assist physicians with diagnosing abnormal heart rhythms, as well as gauging the success of treating these arrhythmias through ablation therapies.

While it is not important to fully understand all the nuances of the field of cardiac electrophysiology, understanding the benefit of this invention does require a basic understanding of how the heart's electrical conduction system works and how some of these arrhythmias are treated.

Cardiac tissue, as it relates to the heart's electrical conduction system, has several important properties. First, a cardiac cell can receive electrical stimulus. Next, it can respond to this stimulus or activate. In the case of cardiac cells, they contract, causing the heart to squeeze and pump blood. In electrical terms, this activation is referred to as depolarization. It is a chemical process in the cell. Once depolarized, the cell needs time, a few milliseconds, to recover. During this repolarization phase, the cell is said to be refractory, meaning it has not fully recovered and cannot yet receive another stimulus. Finally, cardiac cells can propagate that electrical signal; that is, once stimulated, they can in turn stimulate the cells next to them. So, cardiac cells are activated sequentially from an initial point of stimulation, propagating outward, across the heart chamber. The refractoriness of cells just stimulated keeps the wave of depolarization from moving backwards; thus the wave continues forward across cardiac tissue or wall of a heart chamber in an organized fashion. The "pebble-in-a-pond" analogy is often used to describe this; the ripples move outward in an orderly manner from a singular point of stimulation. To build on this, note that, in the heart, some anatomical structures, such as heart valve openings and vessel ostia, will form obstacles for the wave of depolarization to navigate. Also, scars from cardiac surgery or damaged heart muscle do not conduct either, and the wave must make its way around the outside edge of these as well. In the pebble-in-a-pond example, one can imagine scars and heart valves as large rocks protruding from the pond surface; the ripples navigate round them and meet on the other side. That point of stimulation in a normal heart is made up of cardiac cells that have an additional property called automaticity. The chemical makeup of these cells allow them to stimulate themselves—thus starting the wave of depolarization—and then stimulate themselves again and again at a certain pace. Regular cardiac cells do not have this property, so once repolarized and ready, they must simply wait to be stimulated again each time. This continual depolarization and repolarization keeps the heart beating at a regular rate, which is regulated to meet the need the oxygen demands of the body.

In a more macro sense, the heart itself has some features that allow it to depolarize and contract to pump blood in an organized and efficient manner. As shown in FIG. 1, a normal heart beat with a normal electrical pathway (NEP) starts at the Sinoatrial Node near the top of the right atrium (it is the SA node that has those cells with automaticity) and propagates across the right and left atria, causing them to contract and fill the ventricles with blood (a series of one-way valves in the heart prevents the blood from flowing backwards). The upper and lower chambers are divided by the atrioventricular septum which is made of membranous tissue that does not conduct electrical signal. Thus, the wave of depolarization cannot, in a normal heart, simply continue straight across from the atria to the ventricles. This is regulated by tissue at the one electrical channel connecting them. This collection of cardiac cells, called the AV node, has additional properties that cause it to delay depolarization, allowing the atria to completely contract. It then sends the electrical signal straight to the ventricle apices where the wave of depolarization across the ventricles results in an efficient contraction that sends blood to the lungs and the rest of the body. The delay between the atrial and ventricular depolarization causes the distinct "lub-Dup, lub-Dup" sound of the heart.

Electrophysiologists use electrode-tipped catheters placed at various locations in the heart to study its electrical conduction system in order to diagnose cardiac arrhythmias. They generally use well-established methods. The catheters are long thin, plastic tubes with wires inside running to a series of evenly-spaced electrodes or, more commonly, pairs of electrodes at the distal end which are used to record the local activation at that discreet location in the heart. When in contact with the heart wall, a pair of electrodes close together will measure just the electrical activity at that small piece of tissue. A recording system processes these electrograms and displays them on a monitor in real-time and also allows the user to freeze and review them. This allows the user to measure and compare the difference in timing of all the electrograms from the various locations at one moment in time in order deduce the current activation sequence and make a diagnosis.

Multipolar catheters, often with five or ten electrode pairs, are very helpful in analyzing a wave of depolarization across a particular piece of tissue. When such a catheter is positioned against the endocardium (the inside wall of the heart) so that it is oriented along a wave of activation, the delay in activation from one end to the other (distal-to-proximal or proximal-to-distal) will result in a slanted pattern of electrical activations. In FIG. 2A, the wave of depolarization crosses poles 1-2 of this catheter first. A few milliseconds later it crosses electrodes (or "poles") 3-4, then 5-6, and so forth, all the way to poles 19-20, which it crosses last. On this catheter, poles 1-2 are said to be "earliest," and poles 19-20 are said to be "latest." FIG. 2B shows the resulting electrograms. For each heartbeat, or cardiac cycle, the electrogram of poles 1-2 are earliest on the timeline, with poles 2-3 deflecting a few milliseconds later and poles 19-20 the latest. Similarly, it is understood that a wave of depolarization moving in the other direction that crosses poles 19-20 first, followed by poles 17-18, 15-16, and so forth to poles 1-2, wherein poles 19-20 are earliest and poles 1-2 are latest, the visual pattern would be formed by electrograms slanting the other way. Mappings systems, discussed later, describe the timing of electrical activation as a graphical representation in terms of a color scale, where red represents earlier activation and purple represents later activation.

When the multipolar catheter is oriented across the wave of activation, or if there are two intersecting waves of activation, however, the electrograms will have a convex or concave visual pattern to them. In FIG. 3A, the wave crosses the distal and proximal poles 1-2 and 19-20 first, simultaneously, and passes poles 9-10 and 11-12, in the middle, last. The electrograms in FIG. 3B reflect this and form a concave visual pattern. Similarly, with a reverse situation, where poles 9-10 and 11-12 are crossed first and poles 1-2 and 19-20 are crossed last, the resulting electrograms' visual pattern would show a convex curve with poles 9-10 and 11-12 early and poles 1-2 and 19-20 late.

Additionally, there is also a growing variety of special-purpose electrode catheters available. They can produce electrogram patterns that are much more complex and therefore difficult to interpret by electrogram pattern alone, as shown in FIGS. 4A and 4B.

In practice, the use of electrograms to diagnose arrhythmias requires a comprehensive understanding of the heart's anatomy as well as a clear knowledge of a catheter's current position in the heart chamber. Should a physician place the catheter in a different location than he or she thinks, or if it should dislodge after being placed in the correct location, the information provided by its electrograms will be inaccurate, leading to delays or even missed or incorrect diagnoses.

Arrhythmias, in general, can be categorized broadly as focal, reentrant, or disorganized. Focal arrhythmias have a single point of origin. A small group of cardiac cells away from SA node has gained the property of automaticity and depolarize at a fast rate. Since they activate faster than the SA Node, the cells there do not depolarize on their own; the SA Node is "suppressed". Atrial Tachycardia is an example of this. The goal of therapy for this type of arrhythmia is to locate this group of cells depolarizing on their own and deliver localized RF energy (via the tip of an ablation catheter positioned at the site) to "ablate" or destroy them.

Reentrant arrhythmias, in contrast, do not have a single point of origin. The properties of depolarization, repolarization, and refractoriness, can enable a situation where the driving activation pattern forms a loop around a neutral, non-conducting structure such as a heart valve or surgical scar. Once initiated, the wave of depolarization takes it around the neutral structure, either clockwise or counterclockwise, in a circle. Although the wave of depolarization returns to tissue that had just activated as it made the previous loop, that tissue is now past its refractory period and is ready to be stimulated again, in this case by the return wave. The arrhythmia continues on this way, around and around, indefinitely. Atrial Flutter, for example, is a very common reentrant arrhythmia revolving around the tricuspid valve in the right atrium. The therapeutic strategy for reentry is to ablate a line of tissue (again, by means of an ablation catheter) from the neutral structure in the center of the loop to another, nearby neutral structure, thus creating a non-conducting lesion or "line of block" that disrupts the arrhythmia.

While electrograms provided by positioned catheters are helpful in diagnosing an arrhythmia, more precise information is often needed to fully understand the abnormal activation pattern and target the appropriate area for the therapeutic phase of the study, which commences after the diagnosis is made. In many cases, a detailed sampling of electrograms over much or all of the endocardial surface of one or more heart chambers is required.

Electroanatomic mapping systems have been developed to (1) clearly define the endocardial anatomy as a 3D virtual model, (2) record and catalog sampled electrograms, (3) display the activation sequence (or other data) compiled from recorded electrograms on the virtual model, (4) track and display in real-time the current location of electrode catheters in the heart by projecting accurate representations of them into the virtual environment, and (5) record precise locations of sites of interest such as places where RF energy has been applied.

In this two-step procedure—mapping followed by ablation—electrical activity is sensed and measured by advancing a catheter containing one or more electrical sensors into the heart, and acquiring data at a multiplicity of points. These data are then utilized to select the target areas at which ablation is to be performed.

Mapping of the heart or a region thereof typically involves using a mapping catheter with tip and proximal electrodes to record electrical activity in the region of interest. The catheter is moved along the wall of the endocardium during which precise locations and their corresponding electrograms are recorded. Through acquiring new points the three-dimensional anatomic map is created or developed in real-time.

Using the recorded electrograms, local activation times (LATs) are calculated relative to a body surface ECG or a fixed reference catheter. The LAT of each point is the interval between the beginning of the local electrogram of the mapping catheter and the reference signal. Importantly, because points are acquired during the same cardiac rhythm with the identical cycle length, and because the reference catheter or electrogram always remains fixed, the accumulating number of sampled locations and times can be compiled in real-time to accurately describe the activation sequence of one cardiac cycle or heartbeat. The LATs are described in terms of color—red representing the earliest activation so far recorded and purple representing the latest—and applied to an anatomical map of the region of interest to create an activation, or LAT, map. Each new acquisition, or "point," updates the map until a complete—or at least sufficient—understanding of the activation sequence is presented.

FIG. 5 shows a series of new LAT as they are added to a map. Note that the anatomy has already been defined in this example and that the colors update as new data is recorded. The final image shows that a single focal site of activation has been located near the top of the chamber. A sample completed LAT map of Atrial Flutter is shown in FIG. 7A. The red-to-purple color pattern forms a clockwise loop around the tricuspid valve annulus (outlined by a green border), which has been cut out of the map. In this example, the mapping/ablation catheter shown in white, two additional electrode catheters in a darker green, and the site of ablation shown as brown circles, are also visualized.

Additionally, a completed LAT map can be visualized as a "propagation map" where the activation sequence on the map is played by the mapping system as an animation, showing the spread or propagation of electrical activation across the mapped region of interest each time it repeats. This can be a very helpful, dynamic alternative to visually following the rainbow scale of activation around a static LAT map where very slight, yet potentially important changes in color shade, may be missed. FIG. 6 shows a series of screen captures from a propagation map animation of the focal activation sequence shown in FIG. 5. In the animation, the wave in color red of depolarization moves in time across the chamber shown in color blue. Generally, the animations loop continually so the wave can be studied again once it plays through.

During the mapping phase, various parameters may be selected and thresholds set depending on the needs and desires of the electrophysiologist. For example, a "window of interest" (WOI) for assigning activation times on the mapping catheter is selected. This is a time interval relative to an electrogram of a catheter in a fixed location or body surface that has been chosen as "timing reference." Only those activation times falling within this window are acquired. Thus, the WOI serves to limit the choice of electrograms to be measured to only those of the current heartbeat or cardiac cycle. A WOI too wide might include the next or previous cycles. The WOI can also be used in certain situations to exclude extra recordings on the mapping catheter electrogram such "stimulus artifact" from a pacing device, or "farfield signals", including electrograms from another chamber or region that have been detected by the mapping catheter.

Each time a point is acquired, the system searches for an electrogram on the mapping catheter channel within the WOI. A time interval (in milliseconds) between the detected electrograms and the electrogram of the timing reference is calculated. This is recorded as the LAT or local activation time of that point. As the mapping catheter is moved and samples different locations, the timing of these locations varies with how early or late the wave of depolarization crossing the catheter at each particular location is, while in the current heart rhythm. So, the electrograms appear earlier or later compared to those of reference catheter, which remains fixed and, therefore, has the same timing of its electrograms every beat. For this reason, the LATs measured at each new point varies. The points with the lowest, or most negative, LATs are considered earliest and appear in colors red and orange on the LAT map; conversely those with higher or less-negative activation times are later and shade their areas of the map in colors blue and purple. It is the concept of the fixed reference catheter and its "timing reference" that allows the mapped points of many different heartbeats with the same activation sequence to be compiled into a comprehensive LAT map showing the activation sequence of one representative cardiac cycle.

These well-established, highly accurate mapping systems have been developed based on magnetic field sensing. They utilize sensors affixed to the catheter tip to measure the relative strengths of externally-generated magnetic fields and to derive from these measurements the location and orientation of the catheter which are used to very accurately display the distal ends of such "sensor-based catheters" and to create the 3-D anatomical maps representative of the region of interest. Methods for magnetic-based position sensing are disclosed, for example, in U.S. Pat. Nos. 5,391,199, 5,443,489, and 6,788,967 to Ben-Haim, in U.S. Pat. No. 6,690,963 to Ben-Haim, et al., in U.S. Pat. No. 5,558,091 to Acker et al., in U.S. Pat. No. 6,172,499 to Ashe, and in U.S. Pat. No. 6,177,792 to Govari, the entire content of each of which is incorporated herein by reference.

The mapping system may also include visualization of "non-sensor-based catheters" present in the region of interest. Such catheter visualization may display localized electrodes of those catheters, wherein "localization" (location/position detection of electrodes) is obtained through impedance or current-based measurements. For example, impedance is measured between electrodes affixed to the catheter and electrodes placed on the body surface. The position of the catheter and its electrodes is then derived from the impedance measurements. Methods for impedance-based position sensing are disclosed, for example, in U.S. Pat. No. 5,983,126 to Wittkampf, in U.S. Pat. No. 6,456,864 to Swanson, and in U.S. Pat. No. 5,944,022 to Nardella, the entire disclosures of which are incorporated herein by reference.

To summarize, there are two means of visualizing catheters present within region being mapped. Sensor-based catheters use sensors inside the catheter tip to measure the relative strengths of externally-generated magnetic fields and triangulate the location and orientation of the catheter. In contrast, the location and orientation of non-sensor-based catheters are derived from current or impedance measurements between the catheter's own electrodes and externally placed electrodes. The CARTO 3 mapping system, available from Biosense Webster, Inc., employs a hybrid technology of both the magnetic location sensing and current-based data to also provide visualization of both sensor-based and non-sensor-based catheters and their electrodes. The hybrid system, called the Advanced Catheter Location (ACL) feature, is described in U.S. Pat. No. 7,536,218 to Govari et al., the entire disclosure of which is incorporated herein by reference. FIG. 7A is a sample activation map generated by the CARTO 3 mapping system of a right atrium RA of a patient's heart, with visualization of three localized catheters.

The ACL technology is responsive to movement of the electrodes of the catheters and therefore updates the image of the electrodes in real time to provide a dynamic visualization of the catheters and their electrodes correctly positioned, sized, and oriented to the displayed map area on the CARTO 3 mapping system. The catheter visual representations therefore respond to being repositioned by the physician, dislodging from position, and subtler movements such as those caused by the patient's own breathing pattern. This dynamic movement of the catheter images stands in contrast to the 3-D maps themselves, which are created from a set of recorded locations and are, thus, static.

Originally, only the XYZ location of the data points could be used to create and refine the geometry of the chamber being mapped. Called "point by point" mapping, an electrophysiologist would "build out the shell" as he acquired more and more points. More recently, Fast Anatomical Mapping (FAM), a feature on the CARTO 3 mapping system, permits rapid creation of anatomical maps simply by the movement of a magnetic location sensor-based catheter throughout the cardiac chamber. The electrophysiologist can create the 3-D anatomical "shell" of the region of interest as rapidly as he can move the catheter along the wall of the heart chamber, and the electrical activation data may be acquired either simultaneously or after shell creation to create a 3-D electroanatomic map color coded to reveal its electrical activation sequence (or other data). The process of building a map—maneuvering the mapping catheter to numerous locations in the heart chamber to sample the electrical data there—takes time. Sufficient maps of simple arrhythmias can be made in just a few minutes, but more complex arrhythmias may require detailed maps that may take fifteen to thirty minutes or more to create. If the arrhythmia changes or is disrupted, the activation sequence is no longer the same, so new data cannot be added to this map. The electrophysiologist may choose to "remap," in which case the geometry only of the current map is copied to a new map file and new data points in the new heart rhythm may be acquired to color in this "blank canvas." Depending on the size of the region of interest, remapping may take as long to create as the original map, as the sensing catheter is moved from location to location to acquire a new set of LATs.

For the simpler arrhythmias, the electrophysiologist may choose not to remap but merely refer to the electrograms of properly positioned multipolar catheters (for example, see FIGS. 2B and 3B), which, as mentioned earlier, are typically displayed on a recording device during an ablation procedure to provide additional data for use by the electrophysiologist. Electrograms may be particularly informative for those regions or chambers of the heart where there are well-established, standard catheter positions as well as established ablation patterns. An atrial flutter ablation procedure is one of the simplest examples of this. As briefly mentioned earlier, reentrant signals of atrial flutter in the right atrium typically have a circuitous path that is clockwise or counterclockwise around the tricuspid valve annulus TVA. FIG. 7A shows a map of clockwise atrial flutter created using FAM and a dual-purpose, sensor-based mapping and ablation catheter. The red-to-purple color pattern in this map can be traced clockwise around the valve (center circular cutout with thin green border) from the red area in the upper corner all the way around in a loop to the purple area returning to the starting point (CARTO 3 places the brown "early meets late line" into the map automatically between red and purple points). Only one cardiac sequence is described by the map; in reality the wave of depolarization continues around and around in a continuous loop around the TVA. In FIG. 7A, three catheters are visualized. Catheters for this procedure typically include a nonmagnetic, current-based sensing "Duo-deca" multipolar catheter (in green) that enters the right atrium RA from the IVC and is generally positioned in a loop just outside the TVA. Its electrograms, therefore, help describe how the electrical activation is moving around the tricuspid valve. Longer versions of this catheter (actually, ones with more widely-spaced electrode pairs), like the one pictured, can extend across the floor of right atrium (the cavotricuspid isthmus) and into the coronary sinus ostium. A properly positioned Duo-Deca catheter produces a very distinct "slanted" electrogram patterns in atrial flutter (see for example, FIG. 2B). The direction of the slant indicates whether it is clockwise or counterclockwise atrial flutter (for example, clockwise in FIG. 2B). Also visible in this map is the distal tip of a nonmagnetic, current-based HIS catheter (in green) protruding through the TCV from the right atrium RA into the right ventricle RV, and, of course, the magnetic sensing mapping and ablation catheter (in white), shown protruding from the IVC at the cavotricuspid istmus.

The typical ablation pattern for treating atrial flutter is an ablation line across the cavotricuspid isthmus CVI (at the floor of the heart), forming a "line of block" between the tricuspid valve TCV and the inferior vena cava IVC. The map in FIG. 7A shows this as well, as brown circles on the floor of the heart marking ablation sites. When the CVI is ablated, the flutter terminates and the patient's normal heart rhythm will resume. However, it is still necessary to confirm that the ablation line is truly complete because the flutter may terminate when the tissue is merely damaged and not yet truly ablated. This is done by pacing (delivering external electrical stimulus) from a catheter positioned just to the side of the ablation line and observing the resulting activation sequence via the DuoDeca's electrograms. This can also be accomplished by "remapping" the new activation pattern by acquiring new activation points around the valve while still pacing. Here the electrograms' visual pattern will either be a slanted line indicating the line of block is complete and the wave of activation must travel all the way around the valve to depolarize the tissue on the other side of it, or a curved line which suggests that, in addition to traveling up and around the valve, a wave of depolarization is also moving right across the ablation line. The latter reveals there is still more tissue left to ablate to form a complete line of block. FIG. 7B is a map of the same procedure, made during pacing to demonstrate a complete line of block. The pacing stimulus is being delivered to an electrode pole just to right of the ablation line in the color red area of the map. One can trace the resulting activation sequence by following the colors of the rainbow in sequence (red, orange, yellow, green, blue, and purple) starting with red and moving up and around the valve in a counterclockwise fashion all the way to the purple area just to the left of the ablation site, which is the latest tissue activated in the chamber during this pacing maneuver. The map indicates that the line of block is indeed complete. The electrograms of the Duo-deca catheter, from the proximal poles to the ones just leftward of the ablation line would have a slant pattern.

FIGS. 8A and 8B show another example of using the same pacing maneuver to confirm that the ablation line in the CVI is complete. Note the activation pattern in FIG. 8A, where the wave of depolarization, as evidenced by the red-to-purple color pattern of the map, shows activation moving from the red area (at the lower right of the map) not only up and around the top of valve, but also across the ablated line and the floor of the heart, as indicated by the green areas both at the roof and to the left of the ablation line. The latest area of activation in purple is the far wall (at the left of the map). This "split" evidenced by two different green areas shows that there was not a complete line of block and that more ablating was necessary. The electrograms on a duo-deca catheter in this situation would reveal a distinct curved pattern to the electrograms (as shown in FIG. 3B), with both the proximal and distal poles activating earlier than the middle poles. More RF energy was delivered and another remap, FIG. 8B, was again created while pacing to the right of the line. This map clearly shows that now the line of block is complete.

It is not uncommon for an ablation procedure to require several rounds of treatment alternating between ablation and pacing for block assessment before the line of block is deemed completed and successful. If remapping is performed for each block assessment with each remapping for a new set of LATs each taking 5-10 minutes to create, these repeated remappings can greatly lengthen the duration of the ablation procedure. Thus, in the treatment of atrial flutter in the right atrium, for the reasons discussed above, the electrophysiologist may merely rely on the electrograms after each round of ablation without remapping to assess the block It should be noted that one of the understated benefits of using a mapping system is that catheters are visualized without the need of ionizing radiation. Using only fluoroscopy requires that the patient be exposed to radiation to position catheters and continually check their location. In a long procedure, this can add up.

Electrograms of a successful block at the isthmus reveal one or more diagonal lines, each having the same or similar slope, such as item D in FIGS. 9A and 9B. However, electrograms of breakthroughs through incomplete blocks often reveal two diagonal lines with opposite slopes which form either a convex or concave shape depending on the location of the pacing signal, such as items D1 and D2 in FIGS. 9C and 9D. The electrograms in FIG. 9A describe the electrograms generally expected when pacing from the right side of a complete ablation line as in FIGS. 7B and 8B. The concave shape of the electrograms in FIG. 9D, however, indicates the situation in FIG. 8A, where the line of block is not complete (FIGS. 9B and 9C show pacing from the left side of the line, which is occasionally done as well to confirm block from both sides, or "bidirectional block"). FIGS. 10A-10D schematically represent the right atrium with anatomical features of the coronary sinus CS, the superior vena cava SVC and the inferior vena cava IVC. These figures illustrate the locations of the catheters CT and the paths P of the respective electrograms of FIGS. 9A-9D. In FIGS. 10A and 10B, the earliest activation site S and the ablation line A are also shown. In FIGS. 10C and 10D, the breakthrough due to an incomplete ablation line B is shown.

It is understood that the DuoDeca catheter shown in FIG. 7B has more widely-spaced poles—giving a longer span of coverage—than other catheters of the same type. This catheter sits with its poles 1-2, 3-4 and 5-6 actually across the ablation line. While the electrograms in FIG. 9A-9D represent a more standard catheter with all the distal poles positioned to the left of the line, the electrophysiologist will have to know and consider the anatomical location of each catheter and its electrodes when analyzing the EGM pattern. The precise electrogram pattern for situation in FIG. 7B is shown in FIG. 11. Here, activation of poles 1-2, 3-4 and 5-6 (L1), is much earlier because they are on the right side of the ablation line, closer to the site of pacing. The straight, slanted line pattern (L2) made by from poles 19-20 to 7-8 shows the counterclockwise activation up and around the tricuspid and ending at the left side of the line, thus confirming block.

Because experienced electrophysiologists can usually recognize at a glance the electrograms of FIGS. 9A and 9B as complete lines of block, and those of FIGS. 9C and 9D as incomplete lines of block for atrial flutter, they may rely on the electrograms only and chose not to remap after each ablation treatment in order to avoid unnecessarily lengthening the duration of the ablation procedure. However, it would be desirable to provide another means by an electrophysiologist can readily confirm his reading of the electrograms without the need to refresh the activation map. It would be desirable to provide visualization of such other indication of the LATs and/or electrode activation of the catheter for easy reference by the electrophysiologist, and further to provide such visualization on an existing display that is already referenced by the electrophysiologist.

Such desirable features would be particularly advantageous in the diagnosis and treatment of atrial fibrillation (AF), a well-known disorder of the heart, which causes hemodynamic efficiency to be reduced and, in serious cases, can lead to cardiac embolization, stroke, ventricular arrhythmias and other potentially fatal complications. AF can arise from aberrant signals entering the left atrium via the pulmonary veins connected to it. A very common, but rather technically challenging, treatment for AF is a pulmonary vein isolation procedure (PVI), where the cardiac tissue around the ostia of each of the four pulmonary veins in the left atrium is ablated to create a circular line of block preventing these aberrant signals from entering the chamber. Though there are numerous variations of a pulmonary vein isolation employed by electrophysiologists, the common goal is the same. FIG. 12 shows typical left-atrial anatomy with the four pulmonary veins shown in bright colors yellow (right superior), orange (right inferior), purple (left superior) and pink (left inferior). The red structure is the left atrial appendage. Also visualized is the tip of the mapping/ablation catheter as well as brown "point tags" marking ablation sites near the left superior pulmonary vein.

Due to the tubular structure of pulmonary veins, specially-shaped circular mapping catheters (such as Biosense Webster's Lasso catheter, shown visualized by the CARTO mapping system, in FIG. 13) are typically used in the pulmonary veins to analyze electrograms before, during and after ablation procedures. Due to the technical challenges associated with LAT mapping inside the PV, and the fact that the activation sequence changes continuously as more of the tissue is ablated, electrophysiologists almost universally rely on analyzing the Lasso electrograms on the recording system rather than mapping and remapping each change.

As shown in FIG. 13, a lasso catheter (in royal blue) can sit with its distal loop in a pulmonary vein (represented by pink "webbing") with its electrodes in contact with an inner circumference of the vein. The lasso catheter is visualized in an anatomical (anatomy only) CARTO map of the left atrium (the veins have been made transparent by the "webbing"). Other catheters and pink dots marking the current progress of the ablation are also visible. Typically, the size or diameter of the distal loop is adjusted so that the loop and electrodes make adequate contact along the entire inner circumference of the vein in order to sense any aberrant or pacing signals that pass the loop traveling from the LA into the vein or from the vein into the left atrium usually in normal sinus rhythm. Three-dimensional mapping with hybrid localization technology reveals the position of the catheter distal loop and electrodes. However, technical considerations may cause the distal loop to be positioned randomly with its distal and proximal electrodes in any radial orientation. Additionally, since pulmonary veins vary greatly in size, changing the loop diameter to fit properly will also change the association of the loop's distal and proximal electrodes—poles may overlap in small veins or there may be a gap in large veins. FIG. 13 is an example of overlapping electrodes on the lasso catheter. For these reasons, the electrograms alone may reveal which pole(s) are acquiring and the sequence of acquisition but not how this actually correlates to the anatomy itself. For this, the electrophysiologist must cross-reference the electrograms with the 3-D map and the visualized Lasso catheter in order to ascertain the location of acquiring pole(s) relative to the anatomy and hence the location of breakthrough(s) in the ablation line for placement of the ablation catheter.

Although the procedure is a treatment for AF, it is usually performed in normal sinus rhythm to help better gauge the success of lesion formation. As the ablation of tissue around the pulmonary vein ostium proceeds, the electrogram pattern will change on the lasso catheter. In general, the sections that have yet to be ablated will have earlier corresponding electrograms. The ablation of a pulmonary vein is complete when the wave of depolarization across the heart chamber (in the patient's normal heart rhythm) is blocked from entering the vein, and electrograms disappear completely from the Lasso catheter sensing from inside the vein. This process is repeated for each of the four pulmonary veins.

Due to the technical challenge of positioning the mapping/ablation catheter with sufficient contact to create durable lesions at each location around each pulmonary vein ostium, multiple ablations at the same locations are frequently required, and continual analysis of the Lasso electrograms is critical. The electrograms are studied on the recording system to determine the electrode to target, and then those electrodes are located on the visualized lasso catheter in the map.

Mapping systems are very useful for this procedure. Knowledge of each patient's particular anatomy, and especially the orientation and position of the catheters inside it, are crucial. Marking sites of ablation is also very important. However, activation mapping is rarely done. This is because the activation sequence inside each pulmonary vein continuously changes while ablating, and this renders any map made useful for only a brief period of time before a remap is required.

In addition to the changing activation sequence, the Lasso catheter commonly falls out of position or gets dislodged while trying to maneuver the mapping/ablation catheter around in the same space. Repositioning it almost always results in a slightly or greatly different radial orientation than before, meaning its electrodes now represent a different location, and the electrograms and their corresponding positions in the map must be reassessed. For these reasons the following process must be repeated numerous times per procedure. First, once in proper position, the Lasso's electrograms are recorded and analyzed on the recording system. Next, a particular pole is named the current target for ablation. Then the electrophysiologist determines where that pole is located on the catheter image on the mapping system. Finally, he uses the mapping system to position the ablation catheter near that pole to ablate that tissue. After this RF application, as changes in the activation sequence on the Lasso are observed, the process is repeated. The questions, "what's early now?" and "where is that" might be asked several dozen times in a challenging case.

Once, again, it would be desirable to provide an improved means of visualization of the electrode activation of the catheter for easy reference by the electrophysiologist, and further to provide such visualization on an existing display that is already referenced by the electrophysiologist.

Recently, catheters with more complex shapes, such as Biosense Webster's PentaRay catheter shown in FIG. 4A, have become more common. Though helpful for creating LAT maps more quickly by taking multiple points at a time, the PentaRay's electrograms are very difficult to recognize by activation pattern alone (see, for example, FIG. 4B). Here as well, there is a need for this improved means of catheter electrode activation visualization.

Accordingly, there is a desire for a system and method for real-time visualization of electrode activation on a multi-electrode catheter, so a user can instantly recognize signal acquisition by electrodes, including a sequence of electrode acquisition, without reference to electrograms or a 3-D map or wait for any other information. The system and method need not consider any timing reference and may function independently of any mapping or acquisition/propagation maps of any mapping system. However, the system and method may provide visualization of electrode acquisition on a 3-D activation map with LATs information and catheter and electrode localization so that location of any and all acquiring electrodes relative to the mapped region is revealed.

SUMMARY OF THE INVENTION

The present invention includes methods and systems for visualization of electrophysiology information, including intracardiac electrical signals sensed by a catheter. The visualization includes a display of continuous propagation of a catheter's electrogram. An activation sequence is displayed in cine format in realtime or near-realtime and advantageously presented graphically and objectively in the conventional workspace in which an electrophysiologist is already viewing for catheter positioning. Without looking at electrograms, the electrophysiologist may view, for example, an ablation block on a graphical image of a multi-polar "Halo" or "DuoDeca" catheter, earliest activation in a pulmonary vein on a graphical image of a multi-polar "Lasso" catheter, a wave of propagation across a graphical image of a multi-polar "PentaRay" catheter, or a general activation of the coronary sinus on a multi-polar linear catheter. The visualization naturally indicates direction of propagation.

The present invention is directed to methods for visualization of electrophysiology information sensed by electrodes on a catheter, including recording times of electrode signal acquisition, designating a reference electrode signal acquisition, assigning a relative time to each recorded time of electrode signal acquisition relative to the reference electrode signal acquisition, identifying the electrodes with signal acquisition, correlating assigned relative times to identified electrodes to generate a sequence of electrode signal acquisitions, and generating a visual representation of the sequence of electrode signal acquisitions with a graphical image of the electrodes, wherein individual electrodes are visually marked to represent the sequence of electrode signal acquisitions.

In some embodiments, the methods include generating a visual representation with a plurality of images shown in series to represent a progression of the sequence of electrode signal acquisitions. In more detailed embodiments, each image shows a different electrode visually marked, or each image shows at least one different electrode visually marked.

In some embodiments, the catheter has shaft sections extending between adjacent pairs of electrodes, and the methods further includes assigning a relative time to each shaft section in accordance with relative times of its adjacent pair of electrodes, and correlating the relative time of each shaft section with the relative times of its adjacent pair of electrodes, wherein the visual representation includes a series of graphical images of the shaft sections displayed in cine format, and individual shaft section is visually marked in the series of graphical images in accordance with the sequence.

In some embodiments, the methods include adjusting time scale of the visual representation in response to a user's selected time scale and/or adjusting or limiting the ratio of visual representations to actual cardiac cycles in order to facilitate ease of viewing and avoid overlapping sequences of electrode acquisitions.

The present invention is also directed to methods for visualization of electrophysiology information collected by a catheter with a plurality of electrodes, wherein each electrode is adapted to acquire electrical signal, the methods including receiving data on electrode configuration of the catheter, recording times of electrical signal acquisitions by the electrodes, designating an earliest of the electrical signal acquisitions as a reference, assigning a relative time to each recorded time relative to the reference, identifying the electrodes with electrical signal acquisition in accordance with the data on electrode configuration, correlating assigned relative times to identified electrodes to generate a sequence of electrode acquisitions; and generating a visual representation of the sequence of electrode acquisitions, wherein the visual representation includes a series of graphical images of the electrodes and individual electrodes are visually marked to represent the sequence of electrode signal acquisitions.

In some embodiments, the catheter includes shaft subsections, each shaft subsection extending between an adjacent pair of electrodes, and the method further includes assigning a relative time to each shaft section in accordance with relative times of its adjacent pair of acquiring electrodes, and correlating the relative time of each shaft section and the relative times of its adjacent pair of acquiring electrodes, wherein the generating a visual representation includes providing a graphical image of each shaft section, and visually marking individual shaft sections in accordance with the sequence.

In some detailed embodiments, the each shaft subsection is assigned a weighted relative time. The weighted relative time may depend on location of shaft subsection between the adjacent pair of acquiring electrodes. In some detailed embodiments, the electrodes acquiring electrical signal are identified by their lead wires.

The present invention is also directed to systems for collecting and visualizing electrophysiology information. In some embodiments, the system includes a catheter with electrodes adapted to acquire signals, a signal processing unit configured to receive intracardiac signal acquisitions by a plurality of electrodes, and identify the electrodes with intracardiac acquisitions, a timer configured to time the intracardiac signal acquisitions and identify a reference time to an earliest intracardiac signal acquisition, a control unit configured to assign relative times to the intracardiac signal acquisitions relative to the reference time and to correlate assigned relative times to identified electrodes to generate a sequence of signal acquisitions, and a display configured to display the sequence of signal acquisitions in a graphical image of at least the electrodes.

The present invention is also directed to a system for visualizing electrophysiologic data, comprising a signal processing unit configured to receive intracardiac signal acquisitions by a plurality of electrodes, the signal processing unit configured to identify the electrodes with intracardiac signal acquisitions, a timer configured to time the intracardiac signal acquisitions and identify an earliest intracardiac signal acquisition, a control unit configured to assign relative times to the intracardiac signal acquisitions relative to the earliest intracardiac signal acquisition and to correlate assigned relative times to identified electrodes to generate a sequence of signal acquisitions, and a display configured to display the sequence of signal acquisitions in a graphical image of at least the electrodes.

The visual display of the activation sequence may include graphically highlighting the acquiring electrodes and/or shaft sections therebetween by a variety of indicia, for example, color, transparency, size, and/or boldness. The electrodes of one or more catheters may be highlighted in this manner, as desired or appropriate.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

These and other features and advantages of the present invention will be better understood by reference to the following detailed description when considered in conjunction with the accompanying drawings wherein:

FIG. 2B is an electrogram representative of electrode signal acquisition by the catheter of FIG. 2A.

FIG. 3A is a view of a DuoDeca catheter positioned generally transversely to a wave of cardiac cell depolarization.

FIG. 3B is an electrogram representative of electrode signal acquisition by the catheter of FIG. 3A.

FIG. 5 shows a series of new local activation times (LATs) as they are added to a LAT map. Color red shows earliest depolarization, followed by orange, yellow, green, and blue, with purple showing latest depolarization. Dark green highlights catheters. Brown indicates ablation.

FIG. 6 shows a series of screen captures from a propagation map animation of the focal activation sequence shown in FIG. 5. Color red shows wave of depolarization against color blue showing heart anatomy.

FIGS. 9A and 9B are electrograms representative of successful blocks.

FIG. 10A is a schematic illustration of catheter placement for the electrograms of FIG. 9A.

FIG. 10B is a schematic illustration of catheter placement for the electrograms of FIG. 9B.

FIG. 17 is a flowchart implemented by the present invention, according to an embodiment.

FIGS. 18A-18E are tables representative of implementations of portions of the flowchart of FIG. 17.

FIGS. 21A-21I are illustrations representative of a display of a sequence of electrode signal acquisitions, in accordance with yet another embodiment of the present invention.

FIG. 22 is a flowchart implemented by the present invention, in accordance with another embodiment.

DETAILED DESCRIPTION OF THE INVENTION

The present invention is directed to a system and method for real-time visual portrayal of an acquisition sequence of electrodes on a catheter, in particular, real-time visual portrayal of acquisition sequence of electrodes acquiring local activation signals for generating electrograms of a heart. In some embodiments, the visualization of electrode acquisition sequence includes images of the catheter and its electrodes, and visual indicia of electrical propagation along at least an electrical sensing portion of the catheter, including, for example, visual indicia that distinguish acquiring electrode(s) from nonacquiring electrode(s) in real time. In some embodiments, the images include visual indicia of electrical propagation along electrical sensing portions of the catheter, and nonelectrical sensing portion, including, for example, acquiring electrodes and nonconductive tubing extending therebetween. In some embodiments, the visualization of the electrode acquisition sequence includes images of the catheter and its electrodes, superimposed on a heart chamber map, wherein the visualization is dynamic and in real-time corresponding to movement of the catheter in the heart chamber and the heart chamber map is in 3-D and provides anatomical information, as well as any additional information currently available on the CARTO mapping system, such as LAT or voltage, if so desired by the physician.

In a broader perspective, embodiments of the present invention encompass one or more of the following locating and mapping aspects: the first is intended to process locating information; the second processes sensed electrical information; the third integrates previously processed information; and the fourth processes the integrated information to generate a 3-D image of the heart chamber with the catheter superimposed thereon. These aspects, as discussed in U.S. Pat. No. 5,391,199, are described in more detail below.

Catheters will be introduced percutaneously into the heart chambers. Each catheter will be trackable (using the previously described methodology). One or more reference catheters may be left in known landmarks, and a catheter will be used as the mapping/ablation catheter. The locations of the reference catheter(s) will be used to align the location of the heart chamber relative to its location on the "basic image."

Figure 14A:
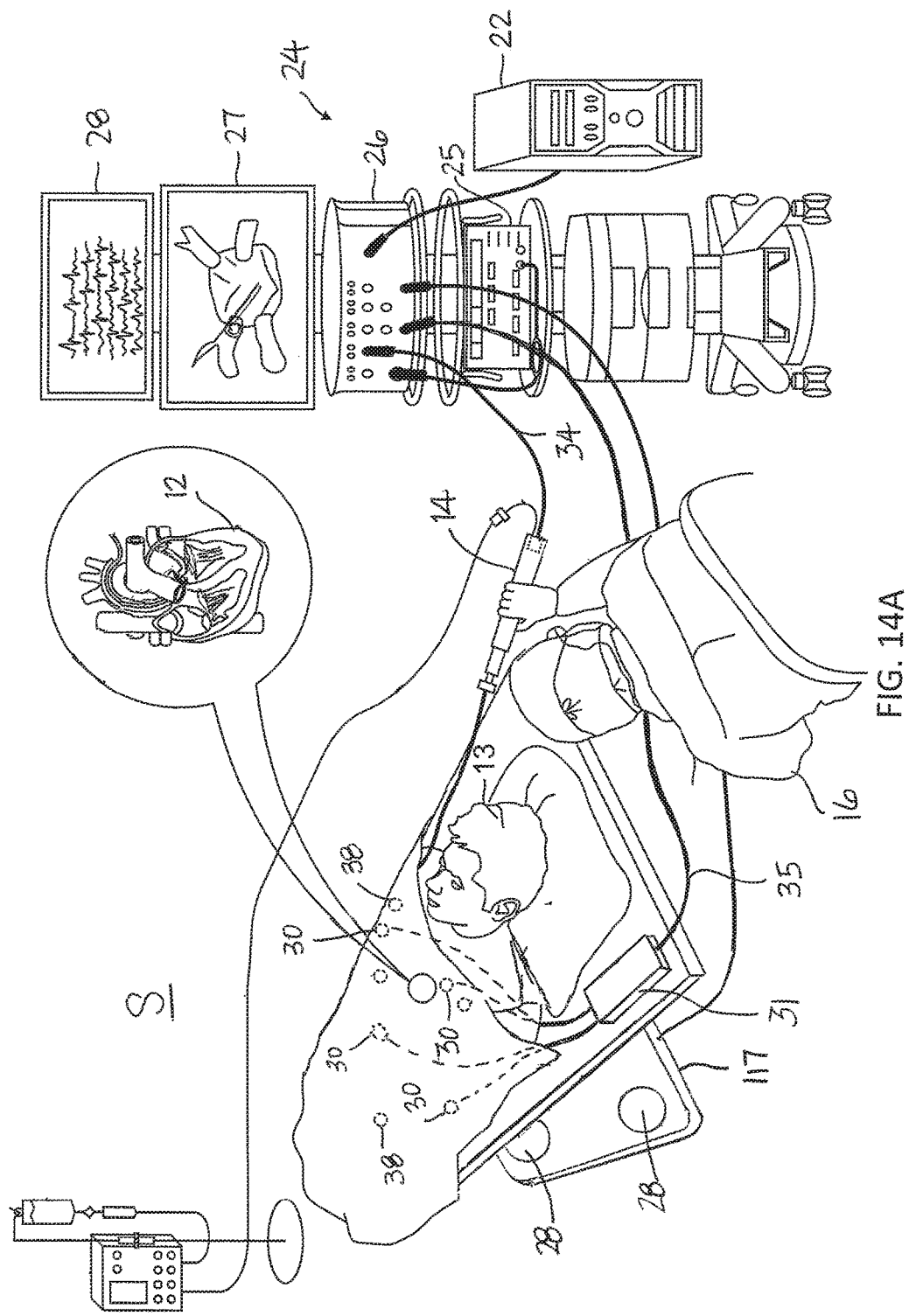
FIG. 14A is a pictorial illustration of a system for performing exemplary catheterization procedures on a heart of a living subject, in accordance with an embodiment of the present invention.

The present invention can perhaps be better understood by making reference to the drawings, starting with FIG. 14A is a pictorial illustration of a system S for performing exemplary catheterization procedures on a heart 12 of a living subject or patient 13, which is constructed and operative in accordance with a disclosed embodiment of the invention. The system comprises a catheter 14, which is percutaneously inserted by an electrophysiologist or operator 16 through the patient's vascular system into a chamber or vascular structure of the heart 12. The catheter 14 has a distal tip carrying a plurality of electrodes, and a control handle by which the operator 16 can manipulate to steer and deflect the catheter.

Electrical activation maps, anatomic positional information, i.e., of the distal portion of the catheter, and other functional images may then be prepared using a console 24, according to the methods disclosed in U.S. Pat. Nos. 6,226,542, and 6,301,496, and in commonly assigned U.S. Pat. No. 6,892,091, whose entire disclosures are herein incorporated by reference. One commercial product embodying elements of the console 24 is the CARTO® 3 System, available from Biosense Webster, Inc., 3333 Diamond Canyon Road, Diamond Bar, Calif. 91765, which performs catheter localization and produces 3-D electroanatomic maps of the heart as required. This system may be modified by those skilled in the art to embody the principles of the invention described herein.

Areas determined to be abnormal, for example by evaluation of electrical activation maps, can be targeted and ablated by application of thermal energy, e.g., by passage of radiofrequency electrical current from a radiofrequency (RF) generator 25 of the console 24 through a cable 34 providing current to the catheter 14, including the ablation electrode 32 at the distal tip, which apply the radiofrequency energy to target tissue. The console 24 typically contains one or more ablation power generators 25, a patient interface unit (PIU) 26, and one or more displays 27 and 28 to display 3-D maps and electrograms. The catheter 14 is adapted to conduct ablative energy to the heart using radiofrequency energy. Such methods are disclosed in commonly assigned U.S. Pat. Nos. 6,814,733, 6,997,924, and 7,156,816, which are herein incorporated by reference. Ablation energy is conveyed from RF generator 25 to the heart 12 through the catheter electrodes via cable 34 which is connected to the console 24. Pacing signals and other control signals may also be conveyed from the console 24 through the cable 34 and the catheter electrodes to the heart 12. Moreover, electrical signals (for example, intracardiac ECG signals) are conveyed from the heart 12 to the console 24 via the catheter electrodes.

As part of the system S, ECG body surface patches, including at least patches 38 are affixed to the patient's body. While the catheter electrodes are sensing intracardiac ECG signals, a plurality of electrodes in the ECG body surface patches 38 measure ECG signals across the heart and torso to provide reference signals for the intracardiac ECG signals measured by the catheter electrodes.

As part of the catheter localization capabilities of the console 24, a magnetic field is generated around the patient 13, for example, by a location pad containing magnetic field generator coils 28 that is placed under the patient. The magnetic fields generated by coils 28 generate electrical signals in coils of an electromagnetic (EM) sensor located in the distal tip of catheter 14. The electrical signals are conveyed to the console 24 which includes a processor or "workstation" 22 that analyzes the signals so as to determine the coordinates of the position and orientation of catheter.

As also part of the catheter localization capabilities of the console 24, the catheter electrodes are connected by lead wires (not shown) in the catheter and the cable 34 to current and voltage measurement circuitry in the processor 22. The processor 22 and the console 24 are also connected by wires and a patch unit 31 to a plurality of body surface electrodes 30, which may be any type of body electrodes known in the art, such as button electrodes, needle electrodes, subcutaneous probes, or patch electrodes. The body surface electrodes 30 are typically in galvanic contact with the body surface of the patient 13 and receive body surface currents therefrom. The body surface electrodes 30 may be adhesive skin patches generically referred to as active current location (ACL patches) and may be placed at any convenient locations on the body surface of the patient 13 in the vicinity of the catheter 14. In the disclosed embodiment, there are six ACL patches 30, three affixed on the anterior surface of the patient's torso and three on the posterior surface. The console 24 comprises voltage generators which are connected to the ACL patches 30 via wires 35 and which the processor 22 uses to measure impedance of the patient tissue at the location of the patches 30. Accordingly, the console 24 uses both magnetic-based position sensing and impedance-based measurements for catheter localization, as described in U.S. Pat. No. 7,536,218, issued to Govari et al., and U.S. Pat. No. 8,478,383, issued to Bar-Tal et al., the entire content of both of which are herein incorporated by reference.

As noted above, the catheter 14 is coupled to the console 24, which enables the operator 16 to observe and regulate the functions of the catheter 14. The processor 22 and/or the console 24 include appropriate signal processing circuits and is coupled to drive a monitor 29 to display visual imagery including the 3-D electroanatomical maps. The signal processing circuits typically receive, amplify, filter and digitize signals from the catheter 14, including signals generated by the catheter electrodes and EM sensor.

Figure 14B:
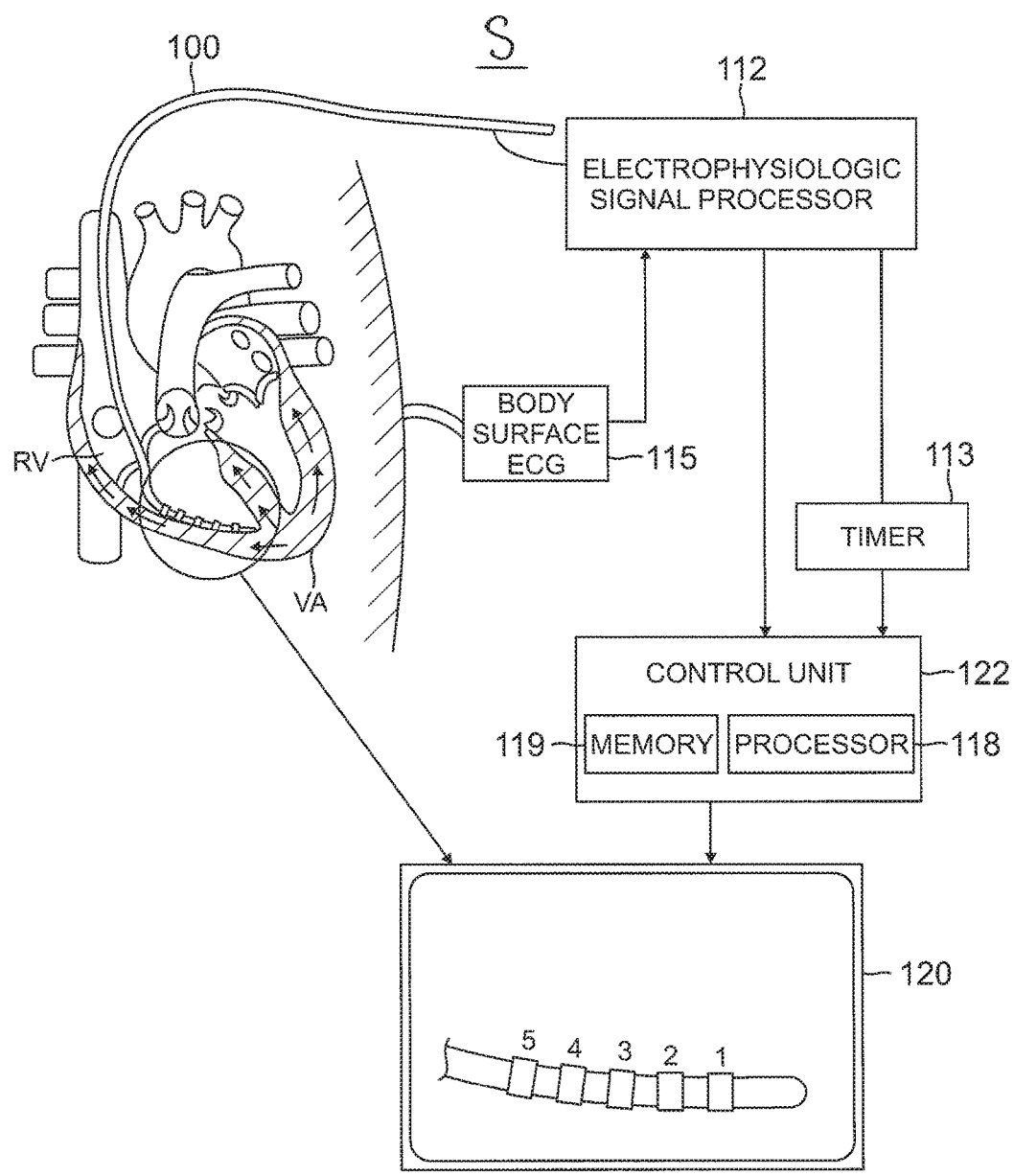
FIG. 14B is a schematic block diagram of the system of FIG. 14A, in accordance one embodiment of the present invention.

FIG. 14B is a schematic block diagram of the system S for displaying electrode acquisition sequence of a linear multipolar catheter 100, in accordance with one embodiment of the present invention. The catheter has electrodes or poles 1-5 which are positioned to detect intracardiac activation sequence, e.g., ventricular tachycardia VT in the right ventricle RV. The local electrograms or signals acquired by poles 1-5 are received by EP signal processor 112 and processed (amplified, digitized, etc.) and sent to a control unit 122 with signal processor 118 and memory 119. The signal processor 112 also identifies the particular electrodes and correlates the particular electrodes with their respective signals and/or local electrograms. The system includes an ECG unit 115 (for example, with body surface electrode patches) for detecting the cardiac cycle in providing reference ECG signals. The system also includes a timer 113 to process timing of occurrences of electrode acquisition, including recording the timing of such occurrences and determining a relative electrode acquisition timing for each electrode that is relative to an earliest occurrence of electrode acquisition within a single cardiac cycle. In accordance with this correlation and relative electrode acquisition timing, the control unit 122 drives the monitor 120 to display visualization of catheter electrode acquisition, including a catheter electrode acquisition sequence in cine. The display includes a 3-D electroanatomical map, including a graphical image of the anatomy mapped.

In accordance with a feature of the present invention, the catheter electrode acquisition sequence is displayed on the monitor 120, wherein the electrodes are visually designated, highlighted or otherwise distinguished, for example, by a color contrasting to a color of the distal tip, as signals are acquired, in the order or sequence of acquisition, within a cardiac cycle. As shown by the intracardiac activation sequence, e.g., VT arrows in the right ventricle RV, the signal travels clockwise from the ventricular apex VA, which is acquired earliest by pole 1, then pole 2, then pole 3, then pole 4 and then pole 5. The acquisition sequence is displayed in animation or cine mode with the graphic image of pole 1 visually marked (FIG. 15A), followed by the graphic image of pole 2 visually marked (FIG. 15B), then the graphic image of pole 3 visually marked (FIG. 15C), then the graphic image of pole 4 visually marked (FIG. 15D), and then the graphic image pole 5 visually marked (FIG. 15E), for a cardiac cycle. Any and all poles activated may remain visually marked for the duration of the cycle, or alternatively, only a single pole may be visually marked during its acquisition and not during another pole acquisition, as shown in FIGS. 15A-15E. The contrasting color visually marking the poles may also be different to indicate relative timing of pole acquisition, much like the color coded time scale of a typical LAT acquisition map wherein colors represent relative timing to a reference time. For example, for FIGS. 15A-15E, pole 1 upon acquisition may be displayed in color red, pole 2 upon acquisition may be displayed in orange, pole 3 upon acquisition may be displayed in yellow, pole 4 upon acquisition may be displayed in green and pole 5 upon acquisition may be displayed in blue.

In another embodiment, nonsensing sections of the shaft between the poles may also be displayed in a manner consistent with the acquisition sequence. For example, as illustrated in FIGS. 19A-19G, shaft section S is visually marked both temporally and spatially between adjacent poles to help visually indicate the direction of acquisition sequence. Where different acquiring poles are highlighted in different colors as discussed above, the color of each shaft section S may be blending of the colors of the adjacent poles. For example, shaft section S1 between poles 1 and 2 may be displayed in reddish orange, as a blending of the color red of pole 1 and the color orange of pole 2.

Figure 8A:
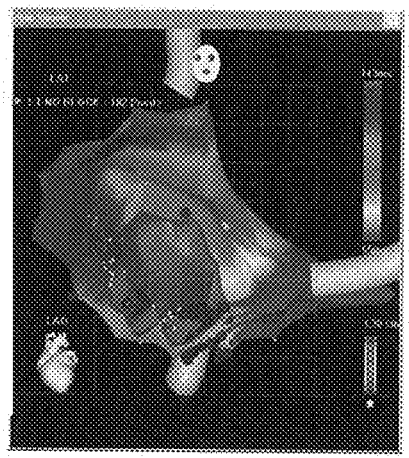
FIG. 8A shows another example of using the same pacing maneuver of FIG. 7B to confirm completion of a CVI ablation line. Color red shows earliest depolarization, followed by orange, yellow, green, and blue, with purple showing latest depolarization.
Figure 8B:
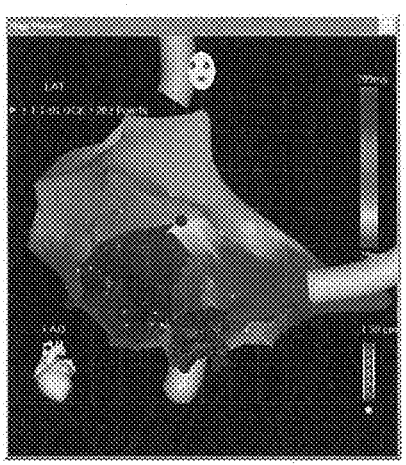
FIG. 8B is a remap of FIG. 8A while pacing to the right of the CVI ablation line, showing line of block is complete. Color red shows earliest depolarization, followed by orange, yellow, green, and blue, with purple showing latest depolarization.
Figure 9C:
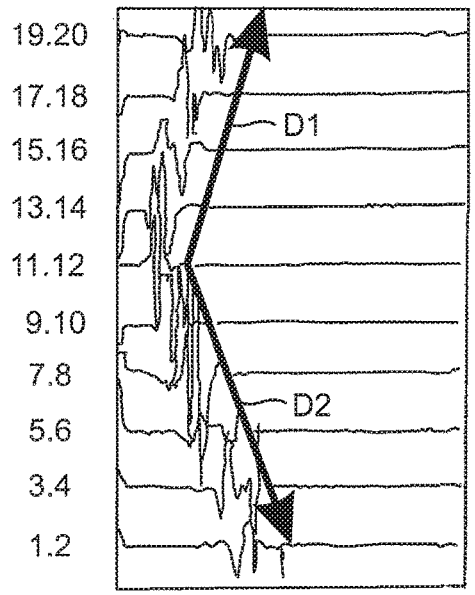
FIGS. 9C and 9D are electrograms representative of incomplete blocks
Figure 9D:
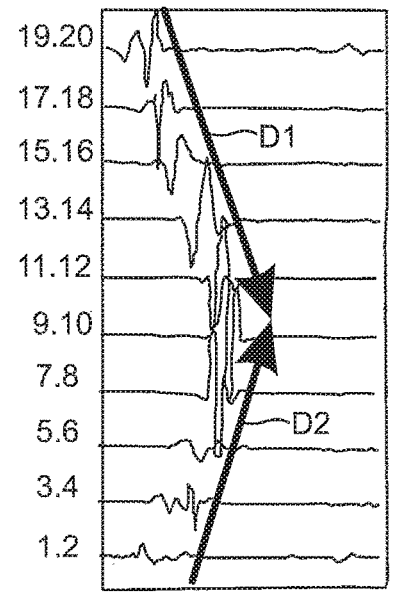
Figure 10C:
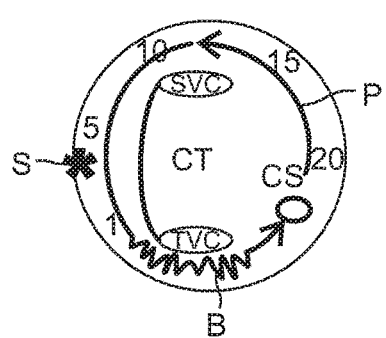
FIG. 10C is a schematic illustration of catheter placement for the electrograms of FIG. 9C.
Figure 10D:
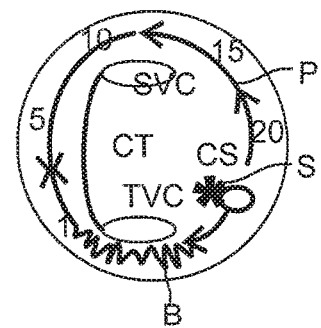
FIG. 10D is a schematic illustration of catheter placement for the electrograms of FIG. 9D.
Figure 12:
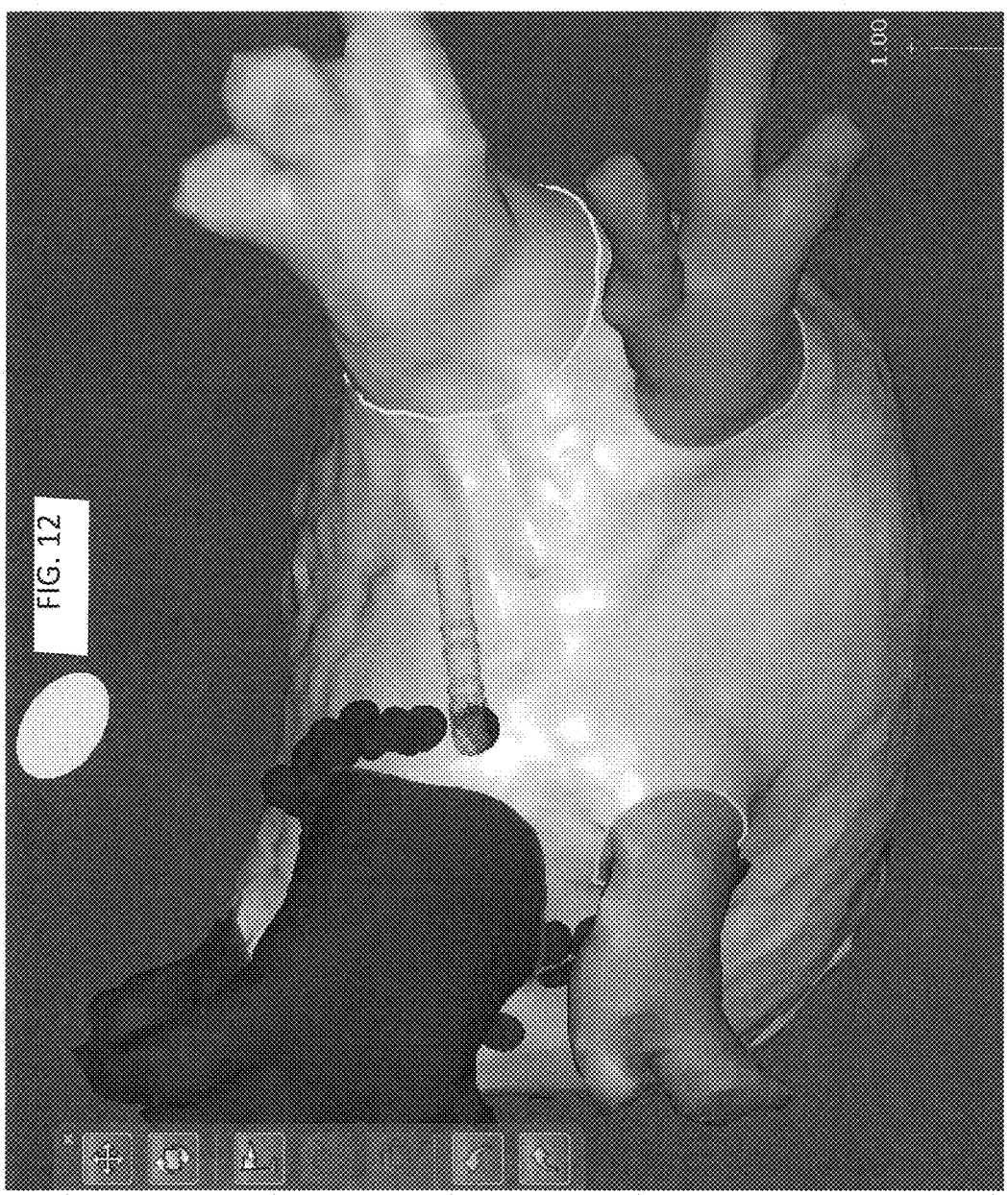
FIG. 12 is a 3-D electroanatomical image of typical left-atrial anatomy with the four pulmonary veins shown in bright colors yellow (right superior), orange (right inferior), purple (left superior) and pink (left inferior).
Figure 13:
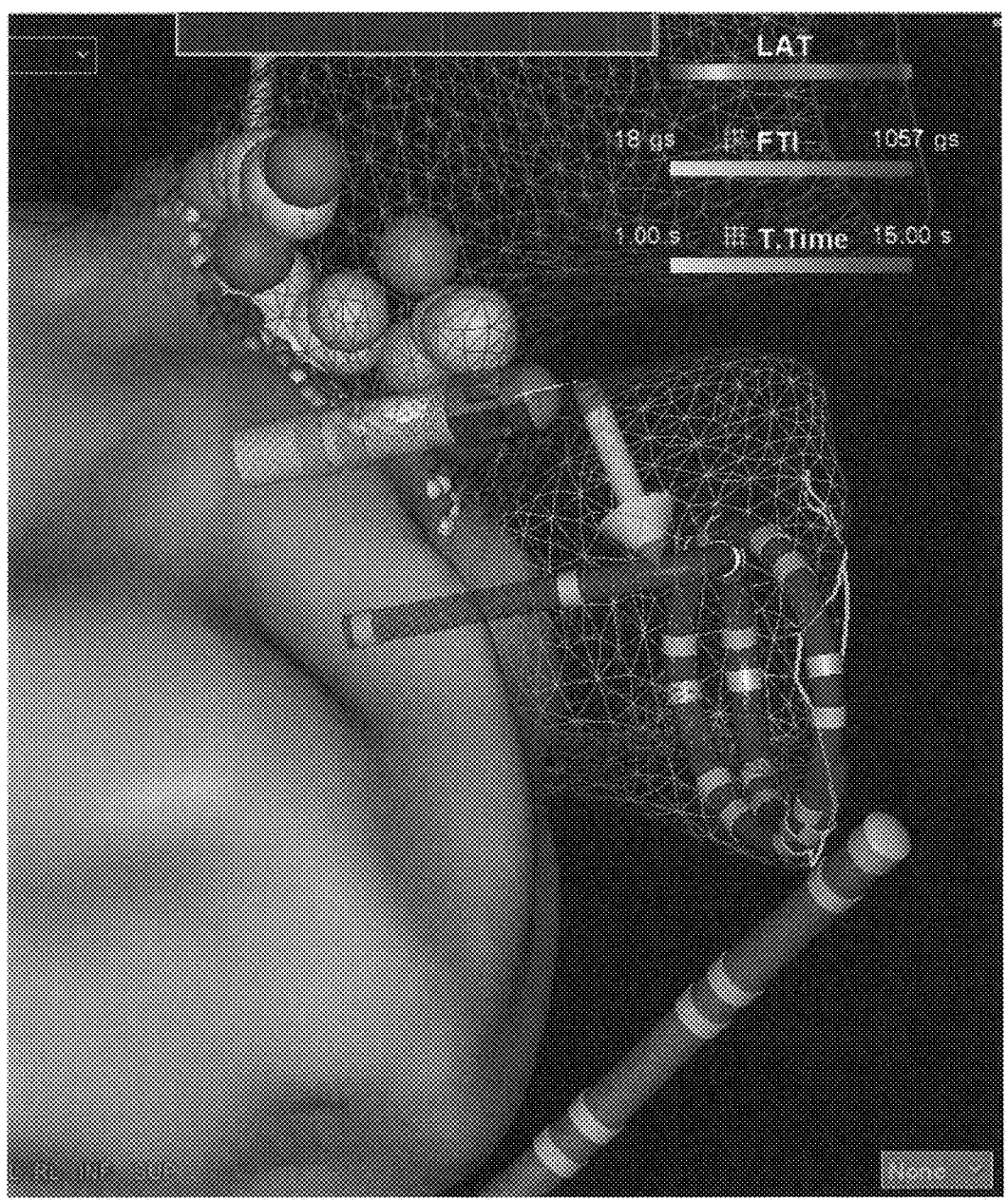
FIG. 13 shows a lasso catheter in color royal blue sitting with its distal loop in a pulmonary vein in pink.
Figures 16A, 16B, 16C, 16D, 16E, 16F, 16G, 16H, 16I:
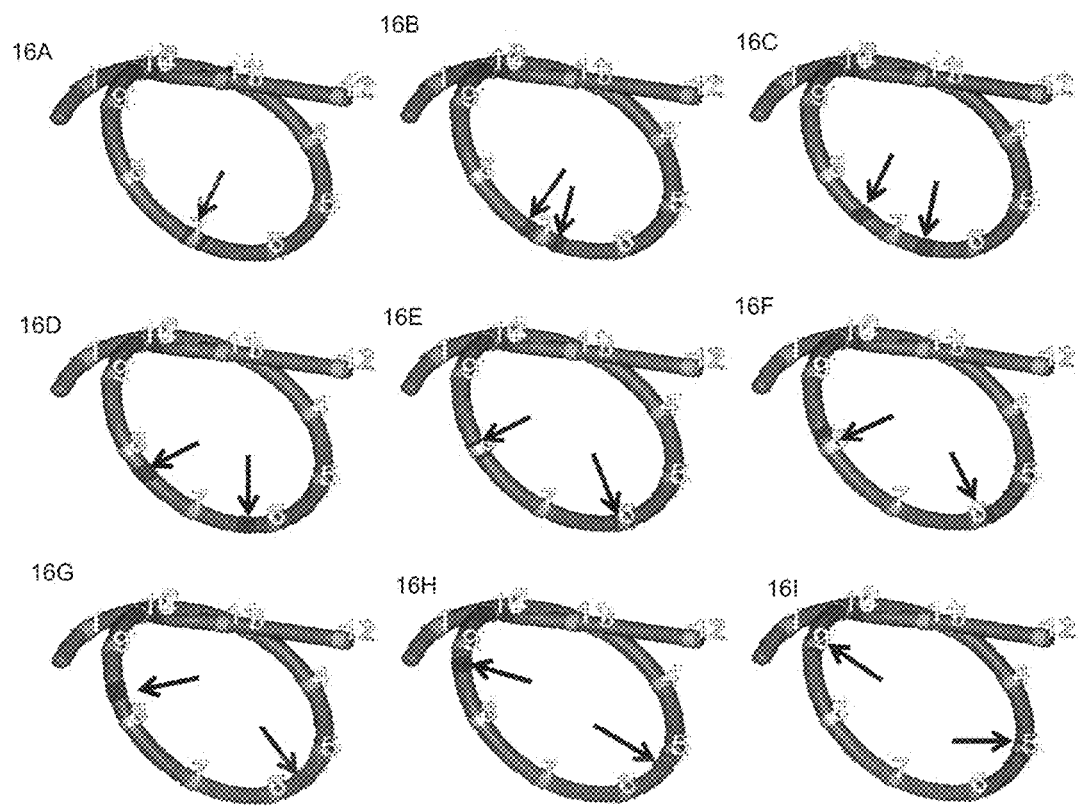
FIGS. 16A-16R are illustrations representative of a display of a sequence of electrode signal acquisitions, in accordance with another embodiment of the present invention. Color green illustrates catheter and color red highlights sequence of signal acquisitions by electrodes and shaft sections therebetween.
Figures 16J, 16K, 16L, 16M, 16N, 16O, 16P, 16Q, 16R:
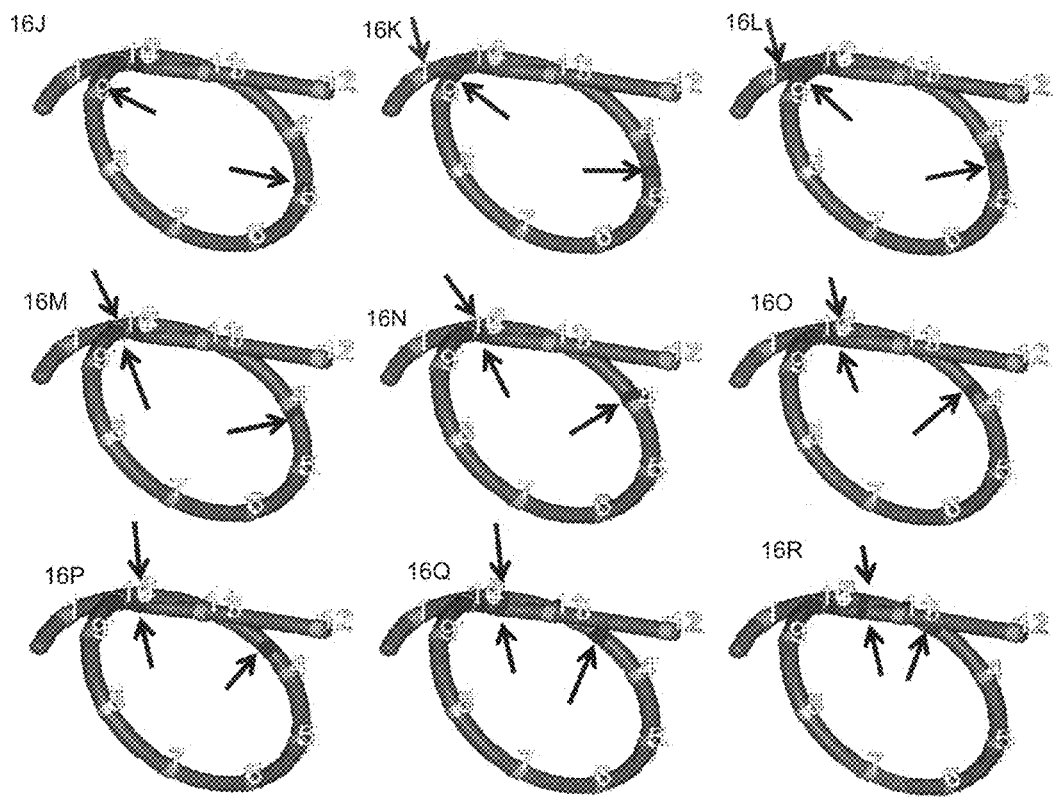

FIGS. 16A-16R illustrate an acquisition sequence where the acquisition sequence has a divergence or split, often indicating an incomplete block, as shown, for example, in FIG. 8A. In FIG. 16A, earliest acquisition occurs at pole 7, followed by poles 6 and 8 as shown in FIG. 16E, followed by poles 5 and 9 in FIG. 16I, and so on and so forth. FIGS. 16B-16D and FIGS. 16F-16H show directions of the acquisition sequence by visual marking of the shaft sections (in color red) between the poles (see arrows).

FIG. 17 illustrates a flowchart representing a method applied by the system S, including the control unit 122 and the processor 119 of FIG. 14, in accordance with one embodiment of the present invention. The method starts at block 200, with the processor 119 receiving and loading parameters of a physical model, as selected by a user, that define physical structure, configuration and properties of a sensing catheter at block 202, including, for example, the type of catheter (linear, circular/lasso, basket, etc.) and location of electrodes on the catheter relative to a reference on or in the catheter. The system then starts electrode acquisition at block 203. This step may include, for example, the provision of a visible or audible indicator indicating the start of the acquisition. At block 203, electrode acquisition of electrical activity within a window of interest occurs in accordance with the discussion provided herein above regarding 3-D mapping, for example, in reference to FIGS. 5 and 6. The electrical activity detected by the electrodes of the catheter may be naturally occurring in the detected tissue in the region of interest or the electrical activity may result from a pacing signal sent to a suitable location in or near the heart chamber where the signal can travel to and/or throughout the region of interest in the heart chamber where the sensing catheter is located. Applying a window of interest limits the recorded signals to only those relevant to the catheter(s) visually representing the electrical activation sequence. In one embodiment, the user selects a specific window of interest for this purpose per block 204. Alternatively, the invention may use the current mapping window of interest already selected for the mapping phase, as described previously. In one (right) branch of the flowchart, timing of occurrences of electrode acquisitions within a window of interest are recorded (block 206) and each occurrence of electrode acquisition is assigned a relative acquisition time that is relative to the timing of an earliest electrode acquisition (block 207). For the sensing catheter with poles 1-5, for example, as shown in FIGS. 15A-15E, where pole 1 acquires earliest at time t(a), followed by pole 2 at later time t(b), followed by pole 3 at later time t(c), and followed by poles 4 and 5 at later times t(d) and t(e), respectively, times t(a)-t(e) are recorded (block 206), and relative acquisition times T(a)-T(e) are assigned (block 207).

In the other (left) branch of the flowchart, identities of the acquiring Poles 1-5 on the catheter are obtained (block 205), for example, by identifying the lead wires on which the acquired signal was transmitted from the catheter to the electrophysiologic signal processor 112, and those identities of poles P1-P5, along with the above assigned relative times of electrode acquisition T(a)-T(e) are then correlated with each other (block 213) to generate a sequence of electrode acquisitions (block 214). An example of the processing of blocks 206, 207, 205, 213 and 214 for the catheter of FIGS. 15A-15E is shown in FIG. 18A.

Figure 15A:
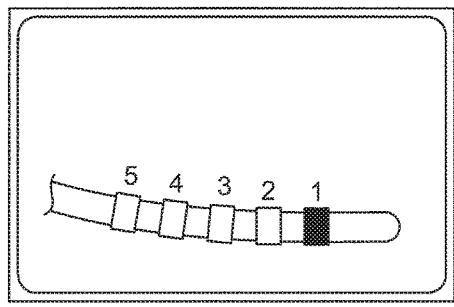
FIGS. 15A-15E are illustrations representative of a display of a sequence of electrode signal acquisitions, in accordance with an embodiment of the present invention.
Figure 15D:
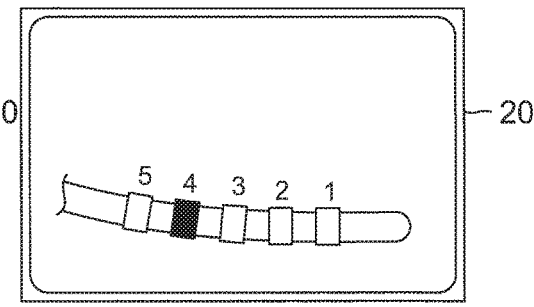
Figure 15B:
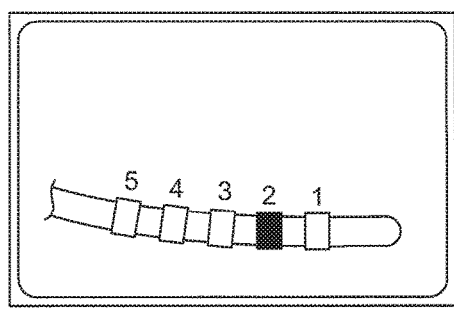
Figure 15E:
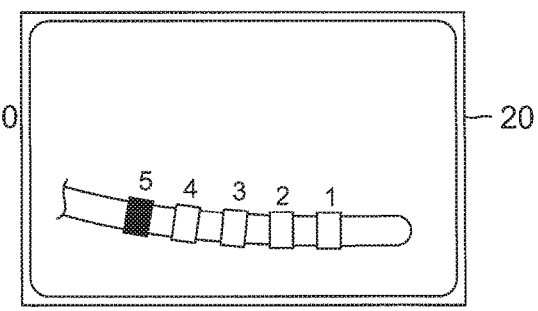
Figure 15C:
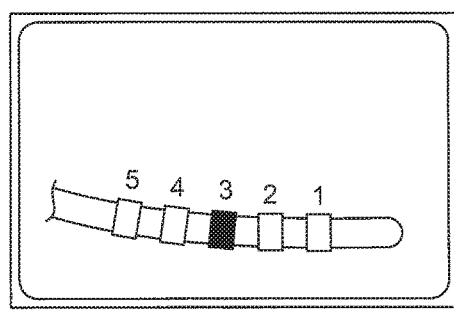

The sequence is then displayed in an animation with a series of graphical images of at least the electrodes which providing visualization of the sequence or order of electrode acquisition per block 215. With reference to FIGS. 15A-15E, the animation reveals an image in cine of five electrodes, with pole 1 highlighted (FIG. 15A), then pole 2 highlighted (FIG. 15B), then pole 3 highlighted (FIG. 15C), then pole 4 highlighted (FIG. 15D), then pole 5 highlighted (FIG. 15E).

Figure 20A:
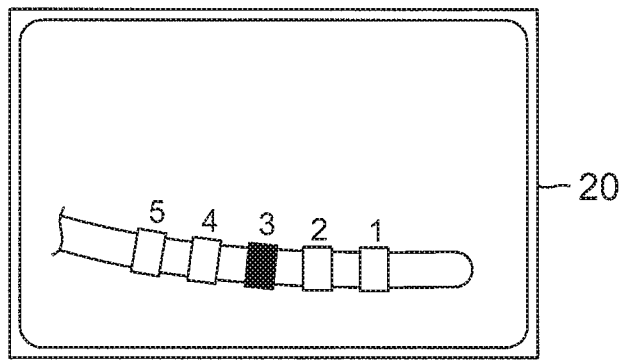
FIGS. 20A-20C are illustrations representative of a display of a sequence of electrode signal acquisitions, in accordance with another embodiment of the present invention.
Figure 20B:
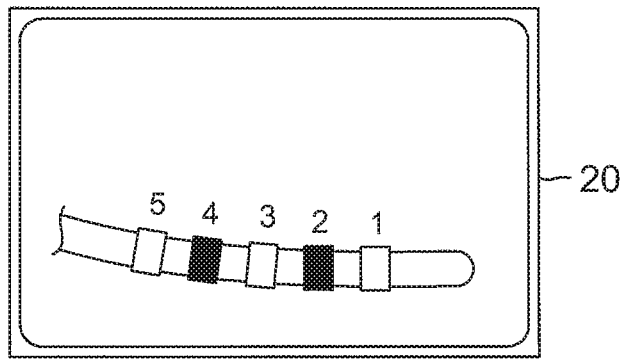
Figure 20C:
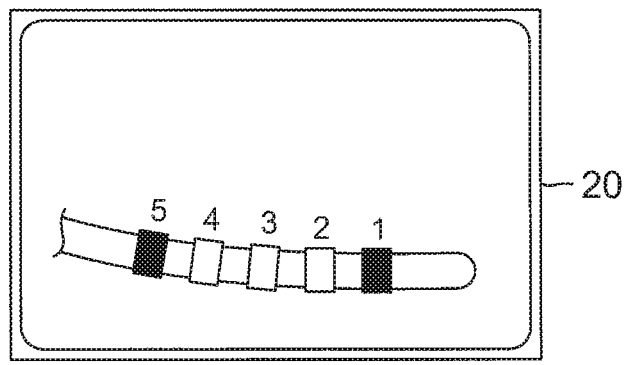

However, for example, if pole 3 of the five-pole catheter acquires earliest at time t(a), followed simultaneously by poles 2 and 4 at time t(b), and followed simultaneously by poles 3 and 5 at time t(c), an example of the processing per blocks 206, 207, 205 and 204 is shown in FIG. 18B. The resulting display sequence per block 215 provides an animation as shown in FIGS. 20A-20C.

Because the entire sequence of electrode acquisition may have a duration on the order of several milliseconds and thus be imperceptible to the human eye, the animation speed may be adjusted. Query 216 of FIG. 17 asks whether a user wishes to adjust the display sequence, for example, by selecting a time scale at which the animation is displayed, per block 218. If no, the processing ends at block 220. If yes, block 218 allows a user to make a selection, whereby, for example, the duration of the animation is increased by a selected factor N by multiplying each relative time T(i) by N, and a re-correlation is performed in block 214 in accordance with the selected time scale. An example of the processing of blocks 214, 216 and 218 is shown in FIG. 18C. As another example in lieu or in addition to block 218, block 219 allows the user to adjust or limit the ratio of visual representations to actual cardiac cycles in order to facilitate ease of viewing and avoid overlapping sequences of electrode acquisitions. The user may select which electrode sequences are displayed, including whether the animation includes the acquisition sequence of every "nth" cardiac cycle. Upon a selection by the user, a re-correlation is performed in block 214.

Figure 19A:
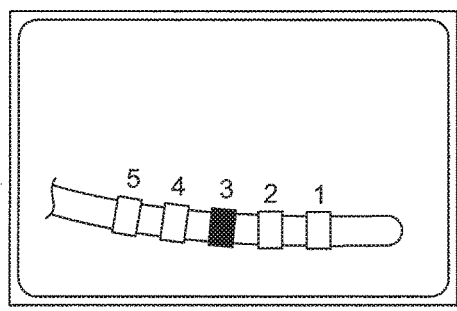
FIGS. 19A-19G are illustrations representative of a display of a sequence of electrode signal acquisitions, in accordance with an embodiment of the present invention.
Figure 19B:
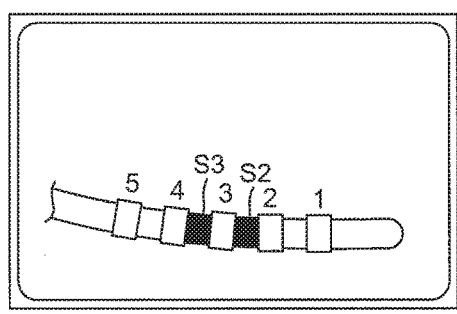
Figure 19C:
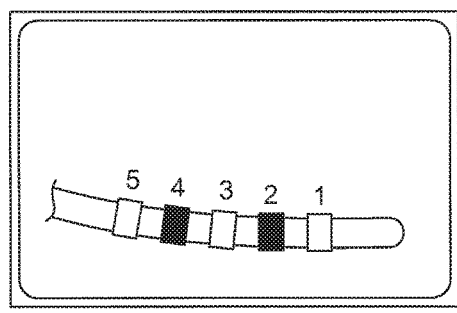
Figure 19D:
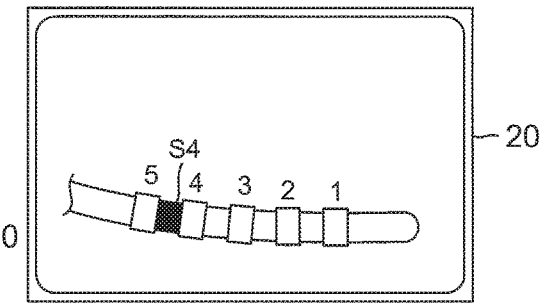
Figure 19E:
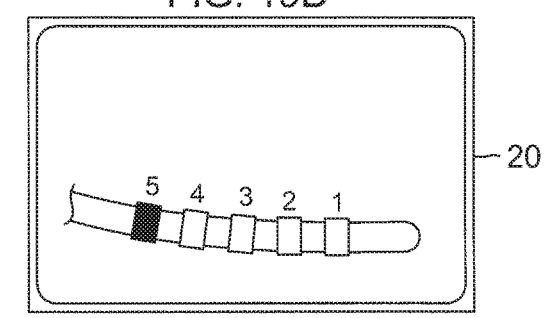
Figure 19F:
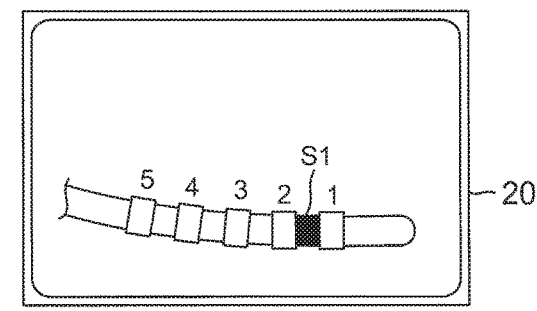
Figure 19G:
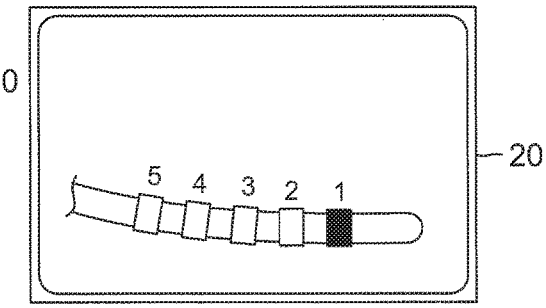

With reference to FIGS. 19A-19G, the animation may also reveal an image in cine of a catheter with five poles P1-P5, wherein the poles and sections of shaft S1-S5 between the poles are both highlighted in accordance with the acquisition sequence and direction of propagation. For example, if pole 3 acquires first, followed by poles 4 and 2, further followed by pole 5 and lastly by pole 1, the image in cine highlights the shaft sections S2 and S3 after highlighting pole 3 (FIGS. 19A and 19B) but before highlighting poles 4 and 2 (FIG. 19C). In this regard, it is understood that the pole acquisition in this example is purposefully asymmetrical outwardly from pole 3 past poles 2 and 4, as pole 5 acquires prior to pole 1. The image in cine thus appropriately highlights the shaft section S4 (FIG. 19D) after highlighting poles 4 and 2 (FIG. 19C) but before highlighting pole 5 (FIG. 19E), and further highlights the shaft section S1 (FIG. 19F) after highlighting pole 5 (FIG. 19E) but before highlighting pole 1 (FIG. 19G).

The shaft section designated per block 209 of FIG. 17 depends on the identity of two poles preceding and their sequence of acquisition. For example, if pole 2 acquires first, followed by pole 3, then the shaft section S2 between poles 2 and 3 is designated, with poles 2 and 3 treated as the adjacent pole pair for the shaft section S2. For example, if pole 3 acquires first, followed simultaneously by poles 2 and 4, then shaft sections S2 and S4 are both designated, with poles 2 and 3 treated as the adjacent pole pair for the shaft section S2, and poles 3 and 4 treated as the adjacent pole pair for the shaft section S4. A relative time T is then assigned for each designated shaft section S per block 210 of FIG. 17. Moreover, the relative time T(Si) assigned to each designated shaft section S may be accomplished by assigning a relative time that is weighted, for example, weighted equally between the relative times of its two adjacent pole pair, for example, averaging the relative times Ti of the two adjacent pole pair, as follows:

$$T(S) = T_{earlier} + (T_{later} - T_{earlier}) * (0.5) \qquad \text{(Eqn. 1)}$$

where $T(S)$=assigned relative time of shaft section between two adjacent poles $T_{earlier}$=assigned relative time of earlier-acquiring adjacent pole $T_{later}$=assigned relative time of later-acquiring adjacent pole An example of processing by block 209 and block 210 (applying Eqn. 1) for shaft sections S is shown in FIG. 18D, which also shows an example of processing by blocks 206, 207 and 205 for poles 1-5, and of processing by blocks 214 and 215 in correlating both the relative times T(i) and T(Si) for the poles and the shaft sections to provide a display sequence as shown in FIGS. 19A-19G.

For the visualization of a catheter wherein adjacent poles are separated by wider shaft sections that can be subdivided for purposes of image cine visual aesthetics into a plurality of subsections Sx, for example, with m subsections, as shown in FIG. 21A-21I, assignment of relative times T(Sx) for these shaft subsections may be accomplished as follows:

$$T(S \times 1) = T_{earlier} + (T_{later} - T_{earlier}) * [1/(m+1)] \quad \text{(Eqn. 2)}$$

$$T(S \times 2) = T_{earlier} + (T_{later} - T_{earlier}) * [2/(m+1)] \quad \text{(Eqn. 3)}$$

$$T(S \times m) = T_{earlier} + (T_{later} - T_{earlier}) * [m/(m+1)] \quad \text{(Eqn. 4)}$$

where T(Sxm)=assigned relative time for shaft subsection m $T_{earlier}$=assigned relative time of earlier-acquiring adjacent pole $T_{later}$=assigned relative time of later-acquiring adjacent pole m=number of subsections In one embodiment, the assigned relative times T(Sxm) for each shaft subsection is weighted according to its location between the earlier- and later-acquiring adjacent poles, and the weighting is applied linearly and dependent on the plurality of subsections between the adjacent poles. An example of the processing of block 209 designating and block 210 (applying Eqns. 2, 3 and 4) assigning relative times for the shaft subsections is shown in FIG. 18E, along with an example of the processing of blocks 206, 207, and 205 for the poles. Per the processing of blocks 214 and 215 correlating both the relative times for the poles and the shaft sections, a display sequence as shown in FIGS. 21A-21I is generated by the system and method of the present invention.

Where the system and method of the present invention also drive the display to reflect position and orientation of the catheter tip in the heart chamber in real time, the process includes spatial electrode localization. In the flowchart of FIG. 22, electrode localization is obtained through measuring position of catheter with a magnetic field sensor typically located in a distal portion of the catheter, per block 208, and determining electrode location based on the magnetic-based measured position, per block 211. Electrode localization is also obtained through impedance of each electrode, which is measured per block 212 to determine the location of the electrode based on an impedance map per block 217.

Location data (magnetic-based and/or impedance-based) is correlated with electrode identity per block 214 and relative electrode acquisition times to drive the display per block 215 in a manner where the graphic image of the catheter and its electrodes move dynamically corresponding to actual movements of the electrodes.

Figure 23:
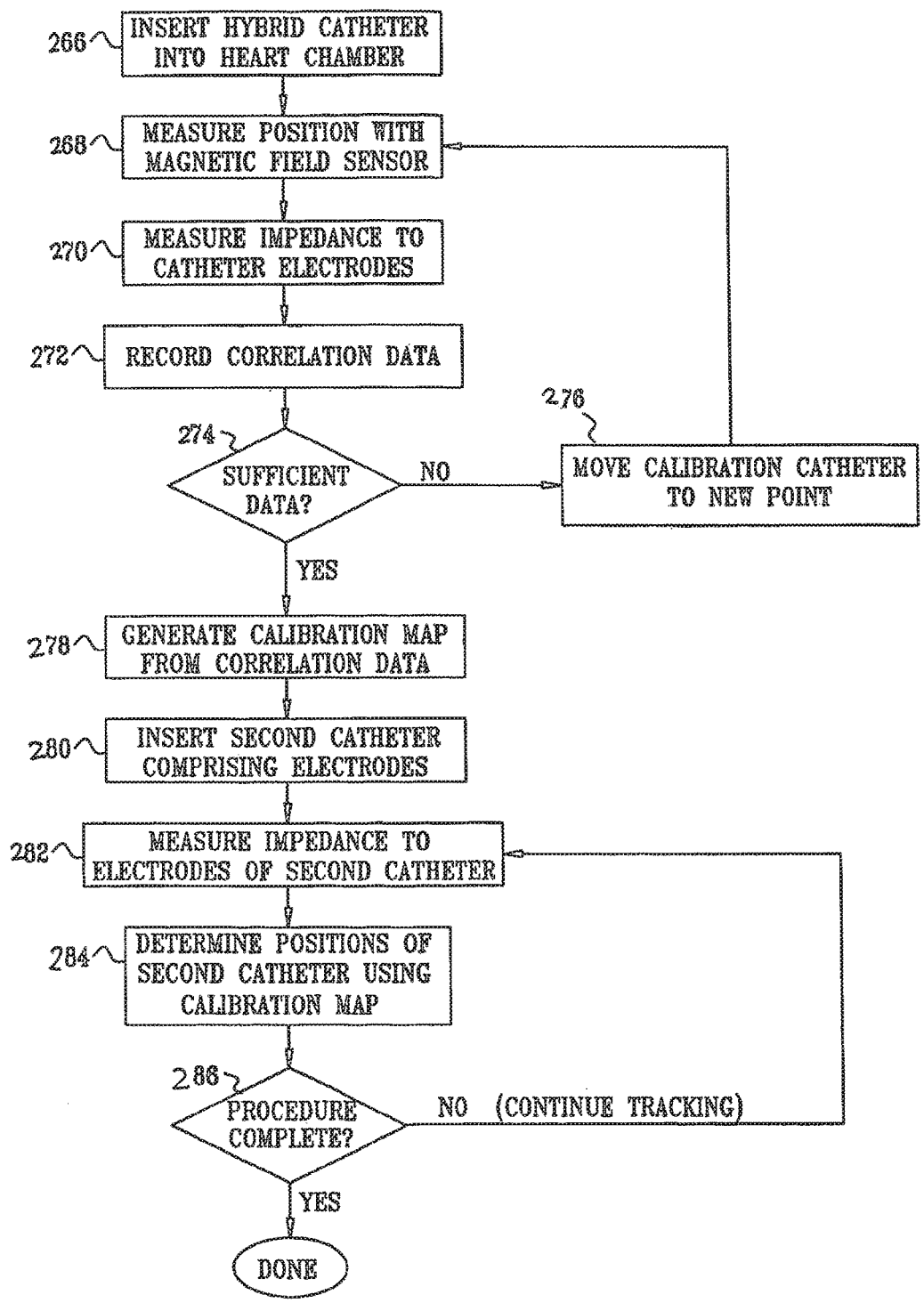
FIG. 23 is a flowchart implemented by the present invention, in accordance with another embodiment.
Figure 25:
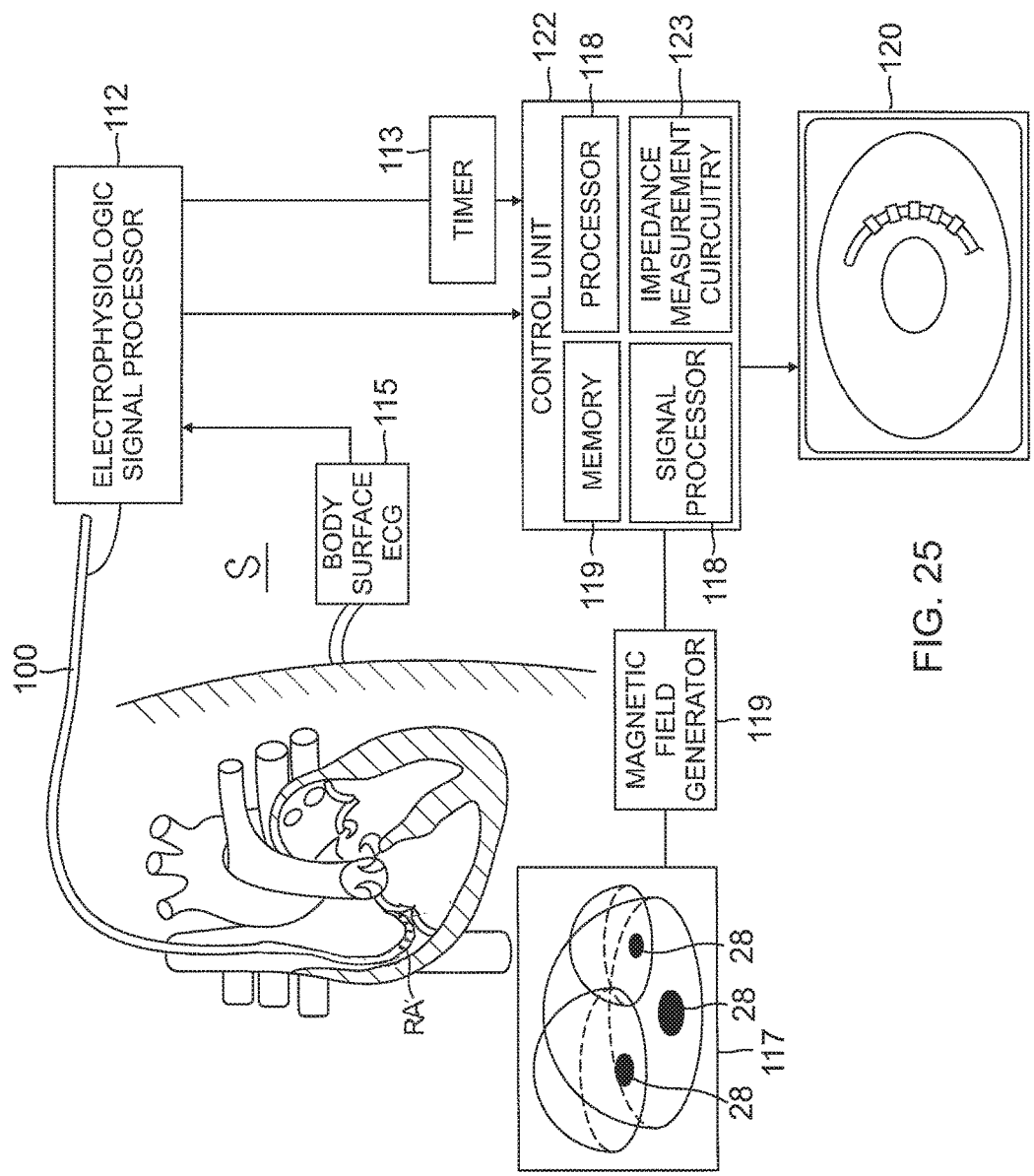
FIG. 25 is a schematic block diagram of the system of FIG. 14A, in accordance another embodiment of the present invention.

Advantageously, the method of visualization of the present invention accommodates hybrid and nonhybrid catheters. Where the sensing catheter is a nonhybrid, magnetic-based catheter, localization of its electrodes are accomplished via blocks 208 and 209. However, where the sensing catheter is a hybrid catheter, an impedance map, and a calibration map on which the impedance map is based may be generated, as shown in the flowchart of FIG. 23, the hybrid catheter has an electromagnetic sensor 22 comprising three coils 24, 26 and 28 which generative electrical signals in response to three magnetic fields generated by magnetic field generator coils G1, G2 and G3, as driven by a magnetic field generator 119, as shown in FIG. 25. The coils G1, G2 and G3 are incorporated in a pad 117 that is situated under the patient. These signals are conveyed to a control unit 122, which analyzes the signals to determine the coordinates of catheter 20. Alternatively, the coils in the magnetic field sensor 22 may be driven to generate magnetic fields, which are detected by coils 28.

Figure 24:
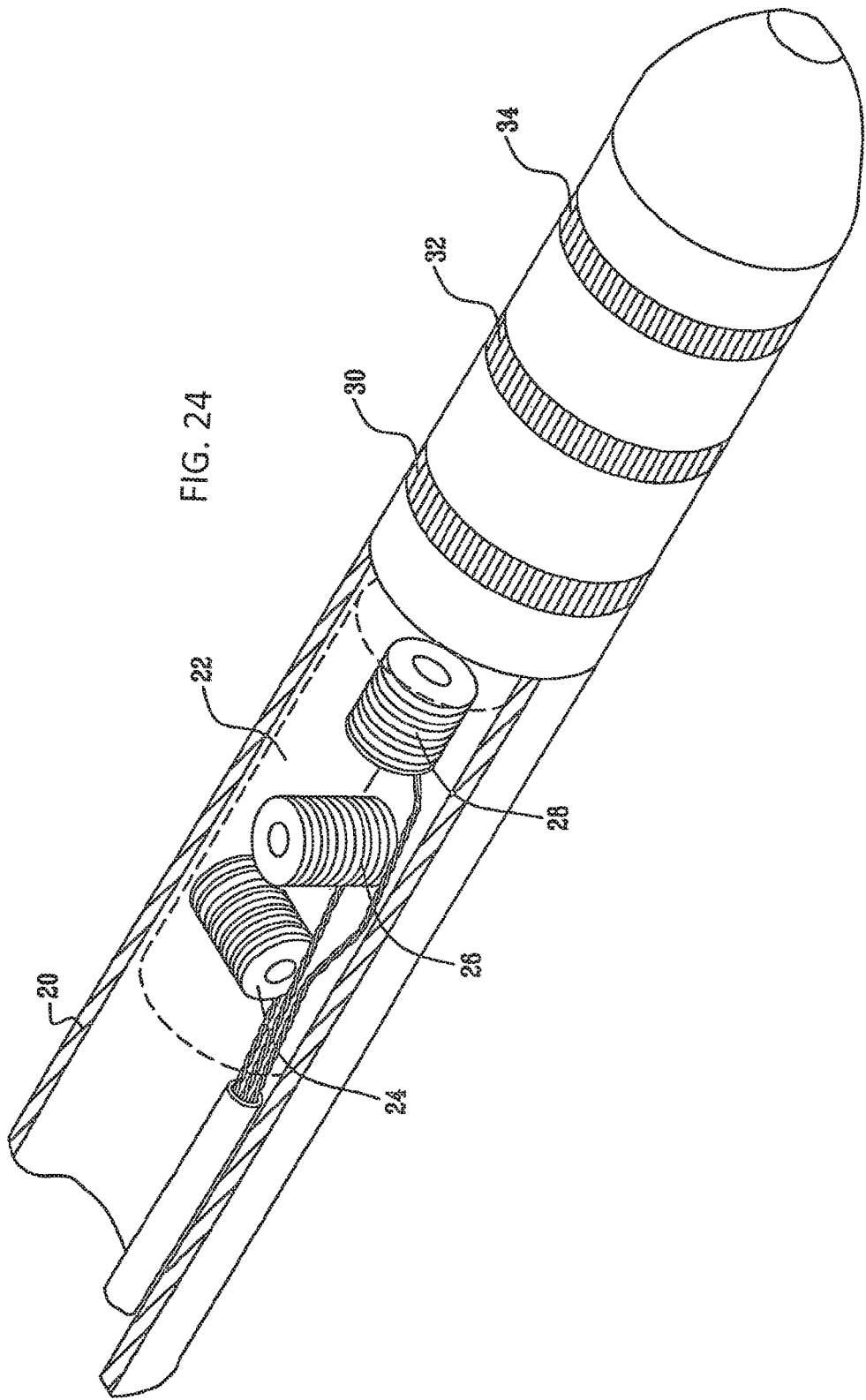
FIG. 24 is a detailed perspective view of a distal tip section, in accordance with one embodiment.

The catheter 20 also carries electrodes 30, 32 and 34, as shown in FIG. 24, whose signals are received by impedance measurement circuitry 123 in control unit 122, as shown in FIG. 25. The control unit 122 is connected by wires to body surface patches via the EP signal processor 112 and body surface ECG unit 115. Impedances between the surface patches and the electrodes 30, 32 and 34 are measured according to methods described in U.S. Pat. No. 7,869,865 to Govari, et al., the entire content of which is hereby incorporated by reference. Control unit 122 drives currents through one or more electric circuits, each of which comprises a catheter electrode, a respective body surface electrode, and the intervening body tissue. By Ohm's law, the impedance between the electrode and patch in each circuit equals the voltage between the electrodes, divided by the current that flows through the circuit. In alternative embodiments of the invention, voltages may be applied across pairs of body surface electrodes, as described by the abovementioned U.S. Pat. No. 5,983,126 to Wittkampf. The respective voltage drops at the catheter electrodes are measured to determine the relative impedances.

Figure 1:
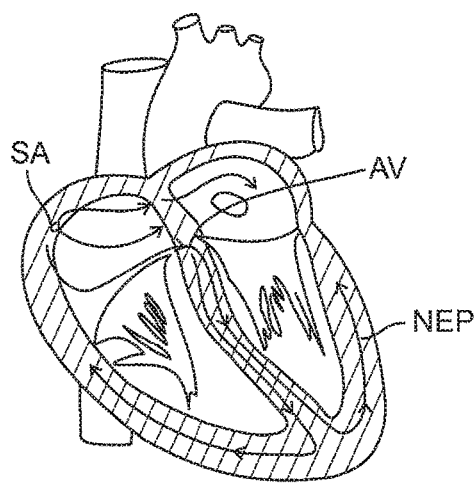
FIG. 1 is a schematic illustration of a heart showing normal electrical pathway.
Figure 26:
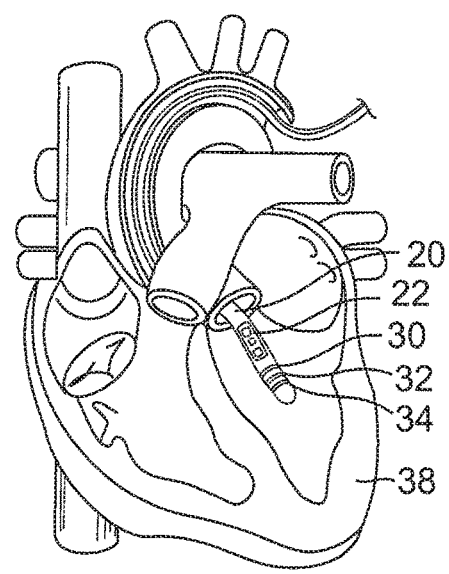
FIG. 26 is a schematic illustration of a heart showing placement of a catheter sensing intracardiac signals.

FIG. 26 is a schematic, pictorial illustration of hybrid catheter 20 positioned within a chamber of heart 38 during generation of a calibration map, in accordance with an embodiment of the present invention. The signals received from magnetic field sensor 22 are used to compute the position and orientation of the catheter at multiple locations, and, in particular, to derive the position coordinates of electrodes 30, 32, and 34 at these locations based on the magnetic coordinate measurements and the known displacement of the electrodes relative to sensor 22. Impedance measurements are also made to electrodes 30, 32, and 34 at the different catheter locations, and these measurements are correlated with the electrode positions as determined by the magnetic position measurements. In this manner a calibration map is generated.

Figure 27:
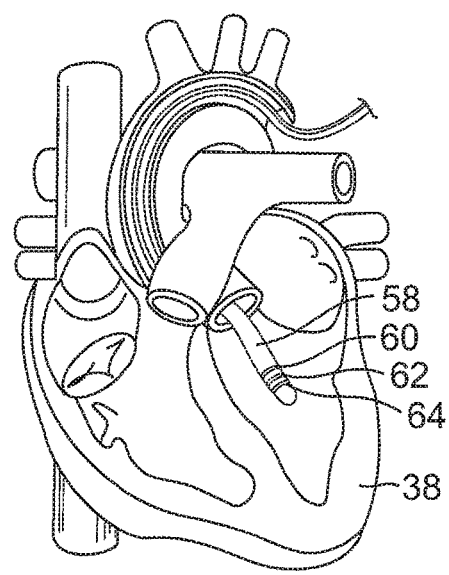
FIG. 27 is a schematic illustration of a heart showing placement of a reference catheter.
Figure 2A:
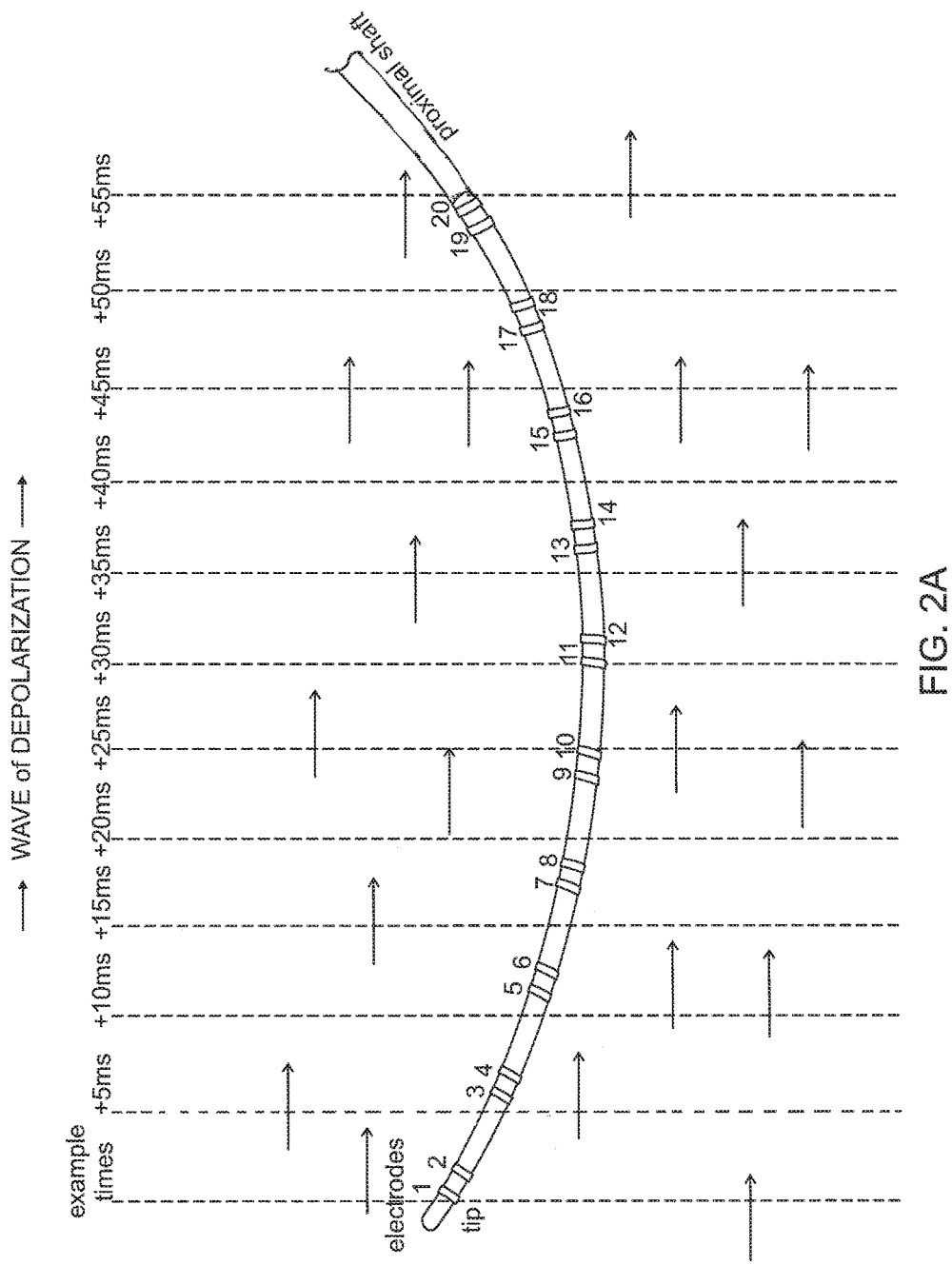
FIG. 2A is a view of a DuoDeca catheter positioned generally parallel with a wave of cardiac cell depolarization.
Figure 4A:
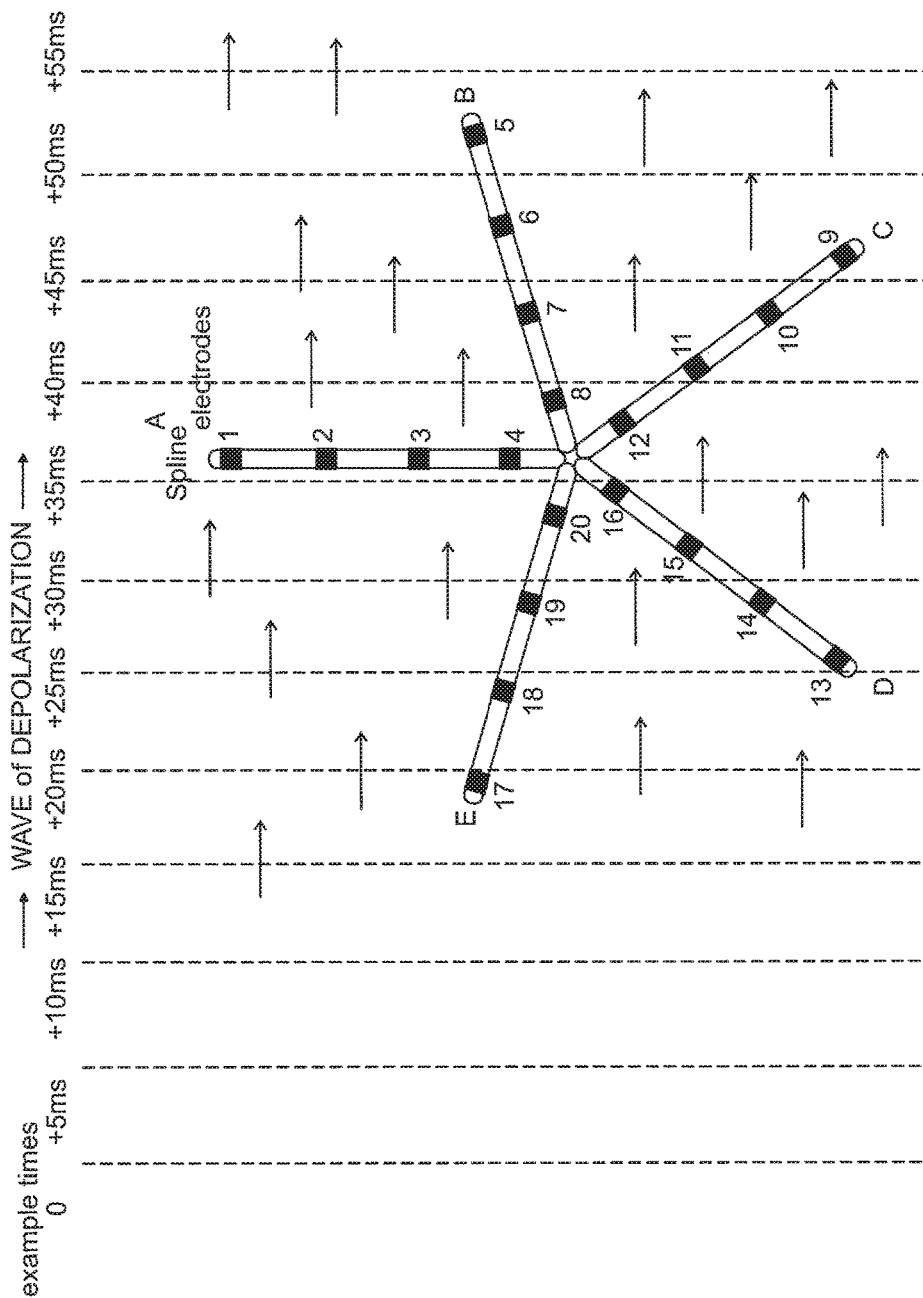
FIG. 4A is a view of a PentaRay catheter positioned in a wave of cardiac cell depolarization.
Figure 4B:
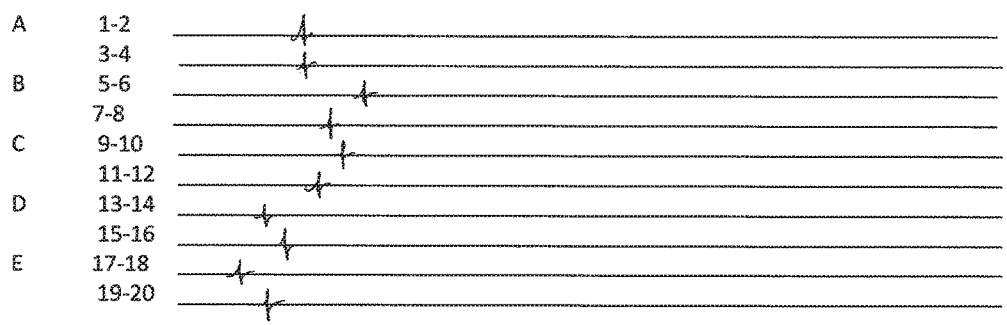
FIG. 4B is an electrogram representative of electrode signal acquisition by the catheter of FIG. 4A
Figure 11:
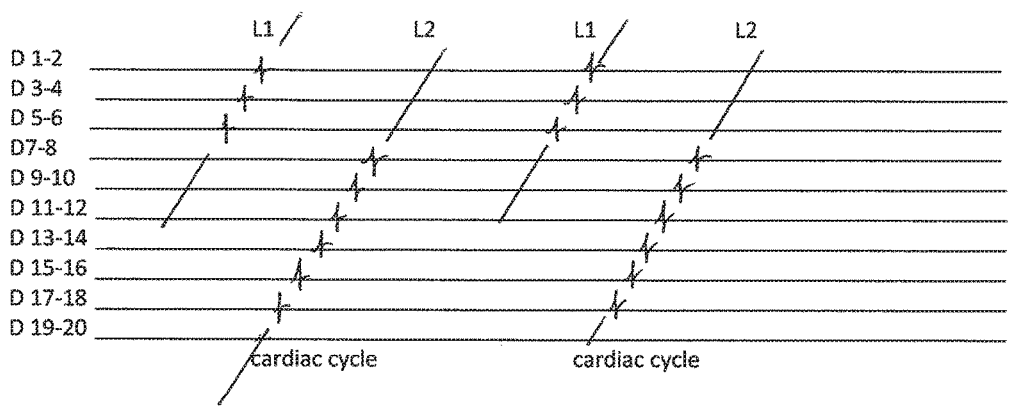
FIG. 11 is an electrogram of the DudoDeca of FIG. 7B
Figure 7A:
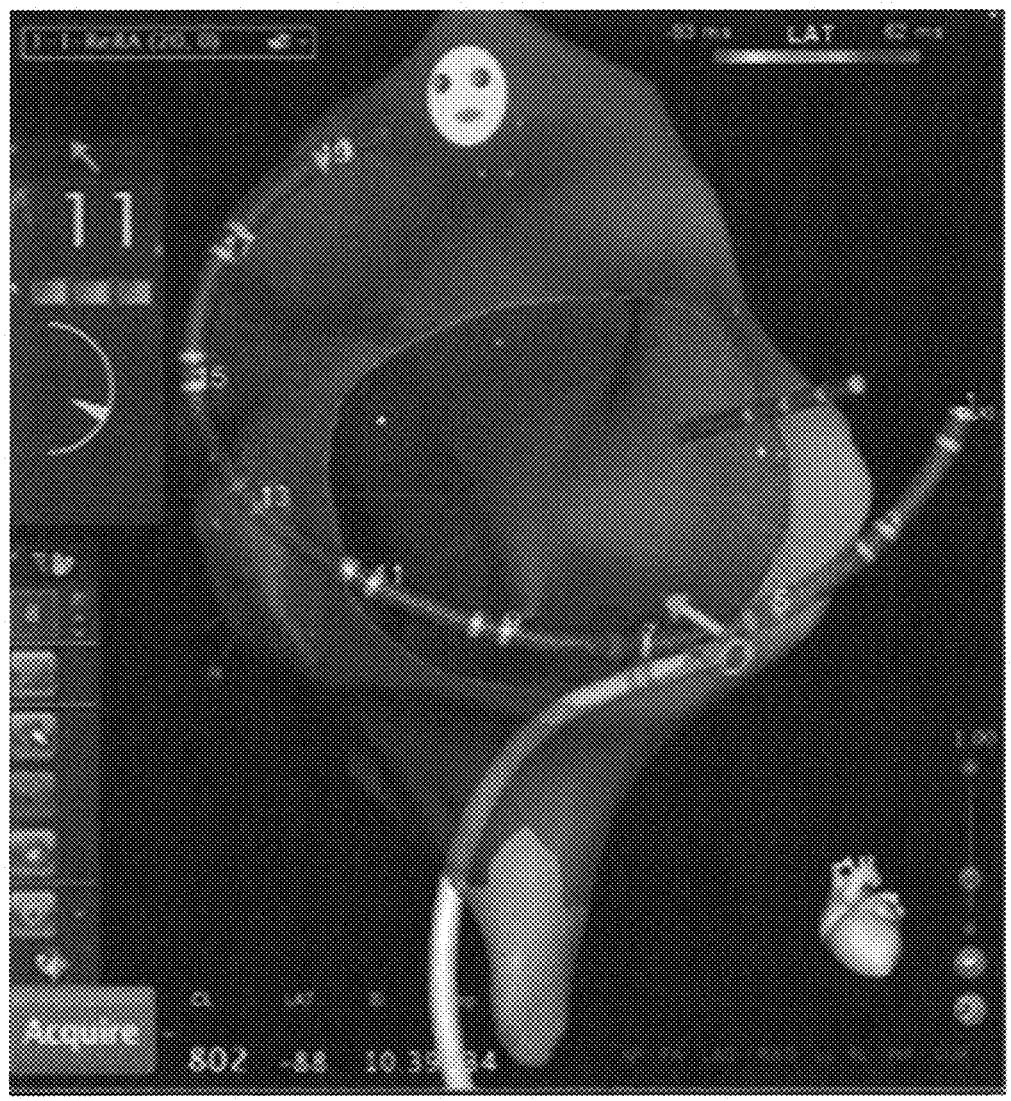
FIG. 7A is a sample completed LAT map of Atrial Flutter based on electrode acquisitions by a DuoDeca catheter. Color red shows earliest depolarization, followed by orange, yellow, green, and blue, with purple showing latest depolarization. Dark green highlights catheters. Brown indicates ablation.
Figure 7B:
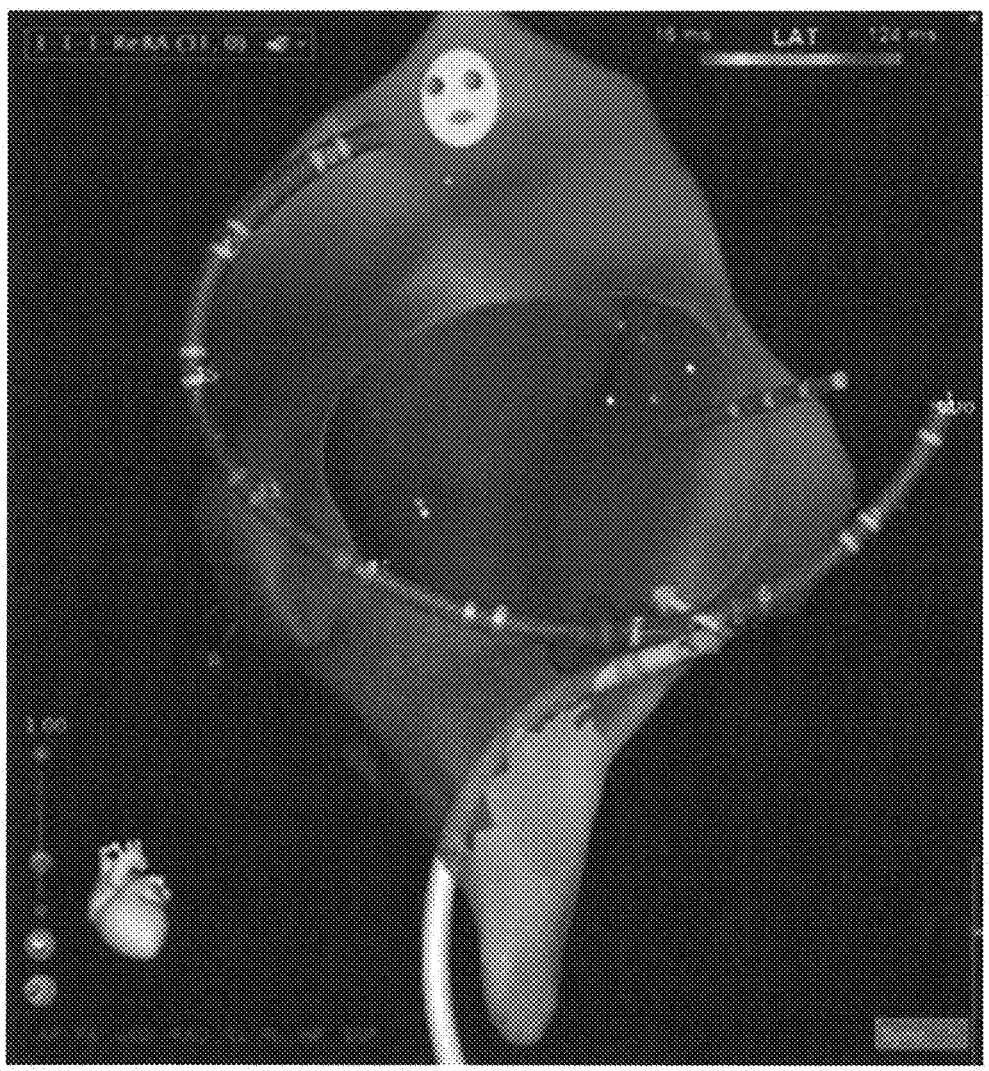
FIG. 7B is a map of the procedure of FIG. 7A, made during pacing to demonstrate a complete line of block. Color red shows earliest depolarization, followed by orange, yellow, green, and blue, with purple showing latest depolarization. Dark green highlights catheters. Brown indicates ablation.

FIG. 27 is a schematic, pictorial illustration of a second catheter 58, which is inserted into heart 38 during or after generation of the calibration map, in accordance with an embodiment of the present invention. As catheter 58 is moved through the heart chamber, impedance measurements taken at electrodes 60, 62, and 64 on the catheter are correlated with the impedance measurements that were previously recorded at known positions on the calibration map. In this manner, the coordinates of catheter 58 are determined accurately, notwithstanding the fluctuations and nonlinearities in the impedance of the subject's body.

FIG. 23 is a flowchart showing a method for generating and applying a calibration map, using tissue impedance, in accordance with an embodiment of the present invention. In an initial step 266, the hybrid catheter 20 is inserted into a chamber of the heart 38. In a magnetic measurement step 268, the magnetic field sensor 22 is used to determine the position coordinates of the catheter, and thus find the specific locations of the catheter electrodes 30, 32 and 34. Impedance measurements at these catheter electrodes are then taken in an impedance measurement step 270. Next, in a correlation step 272, the impedance measurements are correlated with the electrode positions determined in step 268.

In a decision step 274, a determination is made as to whether sufficient data for a calibration map has been collected, based on the needs of the subsequent procedure. If more data is required, the hybrid catheter is moved to a new position in the heart chamber, at a positioning step 276, and steps 268 through 274 are repeated. In practice, steps 268 and 270 are performed continuously, so that steps 266 through 276 may be carried out in a continuous process, as well, while moving the catheter gradually through different parts of the cavity that is to be mapped.

Once sufficient data has been collected, a calibration map is generated in a mapping step 278. Typically, the calibration map comprises a grid of coordinates, determined by magnetic sensing, with a set of impedance measurements (relative to each of the body-surface electrodes or to pairs of body-surface electrodes) recorded at each point in the grid. Alternatively, the grid may be inverted, so that the map indicates the actual, calibrated position coordinates for each set of impedance measurements.

After the calibration map is complete, second catheter 58 is inserted into the body cavity, in an insertion step 280. The second catheter 58 comprises electrodes 60, 62 and 64 that may be used to measure impedances, but it typically lacks magnetic field sensors. In a second impedance measurement step 282, impedances between the electrodes of the second catheter and the body-surface electrodes are measured. In a position sensing step 284, the position coordinates of these catheter electrodes are determined by comparing the measured impedances with the calibration map. Based on the electrode positions, the positions of other elements of the second catheter may also be determined. Steps 282 and 284 may be repeated to continuously track catheter 58, until it is determined that the procedure is done, in a completion step 286.

The preceding description has been presented with reference to presently preferred embodiments of the invention. Workers skilled in the art and technology to which this invention pertains will appreciate that alterations and changes in the described structure may be practiced without meaningfully departing from the principal, spirit and scope of this invention. As understood by one of ordinary skill in the art, the drawings are not necessarily to scale. Also, different features of different embodiments may be combined as needed or appropriate. Moreover, the catheters described herein may be configured to apply various energy forms, including microwave, laser, RF and/or cryogens. Accordingly, the foregoing description should not be read as pertaining only to the precise structures described and illustrated in the accompanying drawings, but rather should be read consistent with and as support to the following claims which are to have their fullest and fair scope.

What is claimed is:
1. A method for visualization of electrophysiology information sensed by electrodes on a catheter, comprising:
    positioning sensing electrodes in contact with cardiac tissue at a plurality of locations to sense conductivity of the cardiac tissue;
    recording times of electrode signal acquisitions;
    identifying the electrodes with signal acquisition;
    detecting a representative cardiac cycle;
    designating a reference electrode signal acquisition for the representative cardiac cycle;
    assigning a relative time to each recorded time of electrode signal acquisition relative to the reference electrode signal acquisition for the representative cardiac cycle;
    correlating assigned relative times to identified electrodes to generate a sequence of electrode signal acquisitions;
    mapping the electrical signal acquisitions relative to the cardiac tissue;
    generating a visual representation on a display with a plurality of separate images shown in series to represent a progression of the sequence of electrode signal acquisitions, each of the plurality of images including a graphical image of the electrodes, wherein individual electrodes are visually marked to represent the sequence of electrode signal acquisitions; and
    energizing ablation electrodes to ablate the cardiac tissue at selected locations to alter the conductivity of the cardiac tissue.

2. The method of claim 1, wherein each of the plurality of separate images shows a different electrode visually marked.

3. The method of claim 1, wherein each of the plurality of separate images shows at least one different electrode visually marked.

4. The method of claim 1, wherein the catheter has shaft sections, each shaft section extending between an adjacent pair of electrodes, the method further comprising:
    assigning a relative time to each shaft section in accordance with relative times of its adjacent pair of electrodes; and
    correlating the relative time of each shaft section with the relative times of its adjacent pair of electrodes,
    wherein the generating a visual representation includes providing a graphical image of each shaft section, and visually marking individual shaft section in accordance with the sequence.

5. The method of claim 1, wherein the identifying the electrodes with signal acquisition includes identifying lead wires of the electrodes.

6. The method of claim 1, wherein data on electrode includes electrode configuration.

7. The method of claim 1, wherein the generating a visual representation on a display of the sequence of electrode acquisitions includes the sequence of electrode acquisitions of one or more cardiac cycle.

8. The method of claim 7, wherein the generating a visual representation on a display includes the sequence of electrode acquisitions of a user's selected cardiac cycle.

9. The method of claim 1, wherein the generating a visual representation on a display is in accordance with a time scale of an animation speed and the method further comprises adjusting the time scale of the visual representation in response to a user's selected time scale.

10. A method for visualization of electrophysiology information collected by a catheter with a plurality of electrodes, wherein each electrode is adapted to acquire electrical signal, the method comprising:
    positioning sensing electrodes in contact with cardiac tissue at a plurality of locations to sense conductivity of the cardiac tissue;
    receiving data on electrode configuration of the catheter;
    recording times of electrical signal acquisitions by the electrodes;
    detecting a cardiac cycle;
    designating an earliest of the electrical signal acquisitions as a reference based on the cardiac cycle;

assigning a relative time to each recorded time relative to the reference based on the cardiac cycle;

identifying the electrodes with electrical signal acquisition in accordance with the data on electrode configuration;

correlating assigned relative times to identified electrodes to generate a sequence of electrode acquisitions based on the cardiac cycle;

mapping the electrical signal acquisitions relative to the cardiac tissue;

generating a visual representation on a display of the sequence of electrode acquisitions, the visual representation including a plurality of separate images shown in series to represent a progression of the sequence of electrode signal acquisitions, each of the plurality of images including a graphical image of the electrodes, wherein individual electrodes are visually marked to represent the sequence of electrode signal acquisitions; and energizing ablation electrodes to ablate the cardiac tissue at selected locations to alter the conductivity of the cardiac tissue.

11. The method of claim 10, wherein the catheter includes shaft sections, each shaft section extending between an adjacent pair of electrodes, the method further comprising:

assigning a relative time to each shaft section in accordance with relative times of its adjacent pair of acquiring electrodes; and correlating the relative time of each shaft section and the relative times of its adjacent pair of acquiring electrodes, wherein the generating a visual representation on a display includes providing a graphical image of each shaft section, and visually marking individual shaft sections in accordance with the sequence.

12. The method of claim 10, wherein the identifying electrodes acquiring electrical signal includes identifying lead wires of electrodes acquiring electrical signals.

13. The method of claim 10, wherein the catheter includes shaft subsections, each shaft subsection extending between an adjacent pair of electrodes, the method further comprising:

assigning a relative time to each shaft subsection in accordance with relative times of its adjacent pair of acquiring electrodes and its location between the adjacent pair; and correlating the relative time of each shaft section and the relative times of its adjacent pair of acquiring electrodes, wherein the generating a visual representation on a display includes providing a graphical image of each shaft section, and visually marking individual shaft sections in accordance with the sequence.

14. The method of claim 13, wherein the assigning a relative time to each shaft subsection includes assigning a weighted relative time.

15. The method of claim 14, wherein the weighted relative time depends on location of shaft subsection between the adjacent pair of acquiring electrodes.

16. A visualization system, comprising:

a catheter with electrodes adapted to acquire signals representative of conductivity of cardiac tissue;

a signal processing unit configured to receive intracardiac signal acquisitions by the electrodes, the signal processing unit configured to identify the electrodes with intracardiac signal acquisitions;

an ECG unit configured to detect a representative cardiac cycle;

a timer configured to time the intracardiac signal acquisitions and identify an earliest intracardiac signal acquisition for the representative cardiac cycle;

a control unit configured to assign relative times to the intracardiac signal acquisitions relative to the earliest intracardiac signal acquisition and to correlate assigned relative times to identified electrodes to generate a sequence of signal acquisitions; and a display configured to display the sequence of signal acquisitions in a series of separate graphical images of at least the electrodes, wherein individual electrodes are visually marked in the graphical images to represent the sequence of electrode signal acquisitions, and wherein the control unit is also configured to map the intracardiac signal acquisitions relative to the cardiac tissue, and energize ablation electrodes to ablate and alter the conductivity of the cardiac tissue at selected locations.

17. The system of claim 16, wherein shaft sections between the electrodes are also visually marked in the separate graphical images to represent the sequence of electrode signal acquisitions.

18. The system of claim 16, wherein assigned relative times are weighted according to locations of the shaft sections.

* * * * *